(12) United States Patent
Yim et al.

(10) Patent No.: US 8,729,245 B2
(45) Date of Patent: May 20, 2014

(54) RECOMBINANT BUTYRYLCHOLINESTERASES AND TRUNCATES THEREOF

(75) Inventors: Kalvin Yim, Annapolis, MD (US); Steven Danso, Bonsall, CA (US); Edward Hausknecht, Annapolis, MD (US)

(73) Assignee: Pharmathene, Inc., Annapolis, MD (US)

( * ) Notice: Subject to any disclaimer, the term of this patent is extended or adjusted under 35 U.S.C. 154(b) by 93 days.

(21) Appl. No.: 13/517,081

(22) PCT Filed: Dec. 21, 2010

(86) PCT No.: PCT/US2010/003225
§ 371 (c)(1), (2), (4) Date: Jun. 19, 2012

(87) PCT Pub. No.: WO2011/084145
PCT Pub. Date: Jul. 14, 2011

(65) Prior Publication Data
US 2012/0252094 A1   Oct. 4, 2012

Related U.S. Application Data

(60) Provisional application No. 61/284,444, filed on Dec. 21, 2009.

(51) Int. Cl.
| | |
|---|---|
| C12Q 1/46 | (2006.01) |
| C07H 1/00 | (2006.01) |
| C12N 15/00 | (2006.01) |
| C12N 15/52 | (2006.01) |
| C12N 15/63 | (2006.01) |
| C12N 15/66 | (2006.01) |
| C07H 21/00 | (2006.01) |
| C07H 21/02 | (2006.01) |
| C07H 21/04 | (2006.01) |

(52) U.S. Cl.
CPC .............. C12N 15/52 (2013.01); *C12N 15/63* (2013.01); *C12N 15/66* (2013.01); *C07H 21/00* (2013.01); *C07H 21/02* (2013.01); *C07H 21/04* (2013.01)
USPC ....... 536/23.1; 435/183; 435/320.1; 435/325; 435/69.1; 506/16; 514/44 R; 536/23.2

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,873,316 A | 10/1989 | Meade et al. | |
| 5,215,909 A | 6/1993 | Soreq | |
| 5,227,301 A | 7/1993 | Turner et al. | |
| 5,304,489 A | 4/1994 | Rosen | |
| 5,322,775 A | 6/1994 | Clark et al. | |
| 5,576,040 A | 11/1996 | Moller et al. | |
| 5,610,053 A | 3/1997 | Chung et al. | |
| 5,633,076 A | 5/1997 | DeBoer et al. | |
| 5,750,172 A | 5/1998 | Meade et al. | |
| 5,756,687 A | 5/1998 | Denman et al. | |
| 5,807,671 A | 9/1998 | Soreq et al. | |
| 5,831,141 A | 11/1998 | Lubon et al. | |
| 5,891,725 A | 4/1999 | Soreq et al. | |
| 5,932,780 A | 8/1999 | Soreq et al. | |
| 5,994,616 A | 11/1999 | Rosen | |
| 6,025,183 A | 2/2000 | Soreq et al. | |
| 6,110,742 A | 8/2000 | Soreq et al. | |
| 6,204,431 B1 | 3/2001 | Prieto et al. | |
| 6,268,487 B1 | 7/2001 | Kutzko et al. | |
| 6,326,139 B1 | 12/2001 | Soreq et al. | |
| 6,580,017 B1 | 6/2003 | Echelard et al. | |
| 6,727,405 B1 | 4/2004 | Gordon et al. | |
| 6,838,076 B2 | 1/2005 | Patton et al. | |
| 6,946,134 B1 | 9/2005 | Rosen | |
| 6,987,211 B1 | 1/2006 | Soreq et al. | |
| 7,078,507 B2 | 7/2006 | Narum et al. | |
| 7,297,680 B2 | 11/2007 | Opstelten et al. | |
| 7,482,013 B2 | 1/2009 | Ballance et al. | |
| 7,572,764 B2 | 8/2009 | Cohen et al. | |
| 2002/0119489 A1 | 8/2002 | Lockridge et al. | |
| 2004/0016005 A1 | 1/2004 | Karatzas et al. | |
| 2004/0147002 A1 | 7/2004 | Cohen et al. | |
| 2005/0112675 A1 | 5/2005 | Kochan et al. | |
| 2008/0213281 A1 | 9/2008 | Watkins et al. | |
| 2009/0169520 A1 | 7/2009 | Soreq et al. | |
| 2009/0208480 A1 | 8/2009 | Huang et al. | |
| 2009/0249503 A1 | 10/2009 | Rosendahl | |
| 2009/0274679 A1 | 11/2009 | Mor et al. | |
| 2009/0286280 A1 | 11/2009 | Roubos et al. | |

FOREIGN PATENT DOCUMENTS

| | | |
|---|---|---|
| EP | 0 361 991 | 4/1990 |
| EP | 0 638 242 | 2/1995 |
| EP | 0 771 874 | 5/1997 |
| IL | 142875 | 4/2001 |

(Continued)

OTHER PUBLICATIONS

Blong et al., Biochemical J. vol. 327, pp. 747-757 (1997).

(Continued)

*Primary Examiner* — Suzanne M Noakes
*Assistant Examiner* — Jae W Lee
(74) *Attorney, Agent, or Firm* — Elliot M. Olstein; Alan J. Grant

(57) ABSTRACT

Isolated nucleic acids encoding polypeptides that exhibit butyrylcholinesterase (BChE) enzyme activity are disclosed, along with molecular criteria for preparing such nucleic acids, including codon optimization. Methods of preparing modified and/or truncated BChE molecules having selected properties, especially selective formation of monomers, are also described. Vectors and cells containing and/or expressing the nucleic acids are also disclosed.

38 Claims, 10 Drawing Sheets

(56) References Cited

FOREIGN PATENT DOCUMENTS

| | | |
|---|---|---|
| WO | WO 88/10118 | 12/1988 |
| WO | WO 94/19935 | 9/1994 |
| WO | WO 95/23158 | 8/1995 |
| WO | WO 96/22379 | 7/1996 |
| WO | WO 99/28463 | 6/1999 |
| WO | WO 99/47661 | 9/1999 |
| WO | WO 00/11208 | 3/2000 |
| WO | WO 00/15772 | 3/2000 |
| WO | WO 00/29608 | 5/2000 |
| WO | WO 00/40693 | 7/2000 |
| WO | WO 00/64957 | 11/2000 |
| WO | WO 00/73427 | 12/2000 |
| WO | WO 01/71014 | 9/2001 |
| WO | WO 02/087624 | 11/2002 |
| WO | WO 2005/035788 | 4/2005 |
| WO | WO 2005/066337 | 7/2005 |
| WO | WO 2006/063055 | 6/2006 |
| WO | WO 2006/137052 | 12/2006 |
| WO | WO 2007/011390 | 1/2007 |
| WO | WO 2007/040568 | 4/2007 |
| WO | WO 2008/019036 | 2/2008 |
| WO | WO 2011/084145 | 7/2011 |

OTHER PUBLICATIONS

Bon et al., J. Biological Chemistry, vol. 272, pp. 3016-3021 (1997).
Cerasoli et al., Extended Abstracts—Chemico-Biological Interactions 157-158, p. 363-365 (2005).
Chilukuri et al., Chemico-Biological Interactions, vol. 157-158, pp. 115-121 (2005).
Cohen et al., Biochem. Journal, vol. 357, pp. 795-802 (2001).
Diamant et al., PNAS, vol. 103, pp. 8628-8633 (2006).
Gibney et al., PNAS, vol. 87, pp. 7546-7550 (1990).
Houdebine et al., Transgenic Research, vol. 9, pp. 305-320 (2000).
Huston et al., PNAS. vol. 85, pp. 5879-5883 (1988).
Keefer et al., Biology of Reproduction, vol. 64, pp. 849-856 (2001).
Keefer et al., Biology of Reproduction, vol. 66, pp. 199-203 (2002).
Kerr et al., Nature Biotechnology, vol. 16, pp. 75-79 (Jan. 1998).
Kolarich et al., Proteomics, vol. 8, pp. 254-263 (2008).
Lockridge et al., J. Biol. Chem., vol. 262, pp. 549-557 (1987).
Lockridge et al., Biochemistry. vol. 36, 786-795 (1997).
Masson et al., J. Biological Chemistry, vol. 268, pp. 14329-14341 (1993).
McTieman et al., PNAS, vol. 84, pp. 6682-6686 (Oct. 1987).
Mehrani, Process Biochemistry, vol. 39, pp. 877-882 (2004).
Morpurgo et al., Bioconjugate Chem., vol. 7, pp. 363-368 (1996).
Nachon et al., Eur. J. Biochem., vol. 269, pp. 630-637 (2002).
Prody et al., PNAS, vol. 84, pp. 3555-3559 (Jun. 1987).
Raymond et al., PLoS ONE, Jan. 17, 2007, 2(1): e162, pp. 1-4.
Robinson et al., PLoS ONE, Mar. 12, 2008, 3(3): e1801, pp. 1-11.
Russell et al., Emerging Infectious Diseases, vol. 10, pp. 674-678 (2004).
Sudo et al., Biochem. Biophys. Res. Comm., vol. 240, pp. 372-375 (1997).
Syed et al., Blood, vol. 89, pp. 3243-3252 (1997).
Urwin et al., Infection and Immunity. vol. 72, pp. 5955-5962 (2004).
Wei et al., Biochemical Pharmacology, vol. 60, pp. 121-126 (2000).
Zbikowska et al., Transgenic Research, vol. 11, pp. 425-435 (2002).
International Search Report for PCT/US2010/03225, Aug. 8, 2011.
Written Opinion for PCT/US2010/03225, Aug. 8, 2011.

Figure 1-1

```
      PacI      EcoRI      NcoI                           ApaI       BclI
      TTAATTAAGAATTCGCCACCATGGCCTGCCCCGGCTTTCTGTGGGCCCTGGTGATCAGCA
  1   ---------+---------+---------+---------+---------+---------+
      AATTAATTCTTAAGCGGTGGTACCGGACGGGGCCGAAAGACACCCGGGACCACTAGTCGT
                        M__A__C__P__G__F__L__W__A__L__V__I__S__T
                        1     3     5     7     9     11    13

CCTGTCTGGAATTTTCTATGGCCGAGGACGACATCATCATTGCCACCAAGAACGGCAAAG
  61  ---------+---------+---------+---------+---------+---------+
      GGACAGACCTTAAAAGATACCGGCTCCTGCTGTAGTAGTAACGGTGGTTCTTGCCGTTTC
       _C__L__E__F__S__M__A__E__D__D__I__I__I__A__T__K__N__G__K__V
         15    17    19    21    23    25    27    29    31    33

TGCGGGGCATGAACCTGACCGTGTTCGGCGGCACCGTGACCGCTTTTCTGGGCATCCCTT
 121  ---------+---------+---------+---------+---------+---------+
      ACGCCCCGTACTTGGACTGGCACAAGCCGCCGTGGCACTGGCGAAAAGACCCGTAGGGAA
       _R__G__M__N__L__T__V__F__G__G__T__V__T__A__F__L__G__I__P__Y
         35    37    39    41    43    45    47    49    51    53

ACGCCCAGCCCCCCCTGGGCCGGCTGAGATTCAAGAAGCCCCAGAGCCTGACCAAGTGGT
 181  ---------+---------+---------+---------+---------+---------+
      TGCGGGTCGGGGGGGACCCGGCCGACTCTAAGTTCTTCGGGGTCTCGGACTGGTTCACCA
       _A__Q__P__P__L__G__R__L__R__F__K__K__P__Q__S__L__T__K__W__S
         55    57    59    61    63    65    67    69    71    73

PvuII
      CCGACATCTGGAACGCCACCAAATACGCCAACAGCTGCTGCCAGAACATCGACCAGAGCT
 241  ---------+---------+---------+---------+---------+---------+
      GGCTGTAGACCTTGCGGTGGTTTATGCGGTTGTCGACGACGGTCTTGTAGCTGGTCTCGA
       _D__I__W__N__A__T__K__Y__A__N__S__C__C__Q__N__I__D__Q__S__F
         75    77    79    81    83    85    87    89    91    93

TCCCCGGCTTCCACGGCAGCGAGATGTGGAACCCCAACACCGACCTGAGCGAGGACTGCC
 301  ---------+---------+---------+---------+---------+---------+
      AGGGGCCGAAGGTGCCGTCGCTCTACACCTTGGGGTTGTGGCTGGACTCGCTCCTGACGG
       _P__G__F__H__G__S__E__M__W__N__P__N__T__D__L__S__E__D__C__L
         95    97    99    101   103   105   107   109   111   113

TGTACCTGAACGTGTGGATTCCCGCCCCTAAGCCCAAGAACGCCACCGTGCTGATCTGGA
 361  ---------+---------+---------+---------+---------+---------+
      ACATGGACTTGCACACCTAAGGGCGGGGATTCGGGTTCTTGCGGTGGCACGACTAGACCT
       _Y__L__N__V__W__I__P__A__P__K__P__K__N__A__T__V__L__I__W__I
         115   117   119   121   123   125   127   129   131   133

TCTACGGCGGAGGCTTCCAGACCGGCACCAGCAGCCTGCACGTGTACGACGGCAAGTTCC
 421  ---------+---------+---------+---------+---------+---------+
      AGATGCCGCCTCCGAAGGTCTGGCCGTGGTCGTCGGACGTGCACATGCTGCCGTTCAAGG
       _Y__G__G__G__F__Q__T__G__T__S__S__L__H__V__Y__D__G__K__F__L
         135   137   139   141   143   145   147   149   151   153
```

Figure 1-2

```
                                                                NarI
                                                                KasI
         TGGCCAGAGTGGAACGCGTGATCGTGGTGTCCATGAACTACAGAGTGGGCGCCCTGGGCT
481      ---------+---------+---------+---------+---------+---------+
         ACCGGTCTCACCTTGCGCACTAGCACCACAGGTACTTGATGTCTCACCCGCGGGACCCGA
          A   R   V   E   R   V   I   V   V   S   M   N   Y   R   V   G   A   L   G   F
           155     157     159     161     163     165     167     169     171     173

PvuII
                                                                         PflMI
         TCCTGGCTCTGCCCGGAAATCCCGAGGCCCCTGGCAACATGGGCCTGTTCGACCAGCAGC
541      ---------+---------+---------+---------+---------+---------+
         AGGACCGAGACGGGCCTTTAGGGCTCCGGGGACCGTTGTACCCGGACAAGCTGGTCGTCG
          L   A   L   P   G   N   P   E   A   P   G   N   M   G   L   F   D   Q   Q   L
           175     177     179     181     183     185     187     189     191     193

PstI
         TGGCCCTGCAGTGGGTGCAGAAGAATATCGCCGCCTTCGGCGGCAACCCCAAGAGCGTGA
601      ---------+---------+---------+---------+---------+---------+
         ACCGGGACGTCACCCACGTCTTCTTATAGCGGCGGAAGCCGCCGTTGGGGTTCTCGCACT
          A   L   Q   W   V   Q   K   N   I   A   A   F   G   G   N   P   K   S   V   T
           195     197     199     201     203     205     207     209     211     213

CCCTGTTTGGCGAGTCTGCCGGCGCTGCCAGCGTGTCCCTGCATCTGCTGAGCCCTGGCA
661      ---------+---------+---------+---------+---------+---------+
         GGGACAAACCGCTCAGACGGCCGCGACGGTCGCACAGGGACGTAGACGACTCGGGACCGT
          L   F   G   E   S   A   G   A   A   S   V   S   L   H   L   L   S   P   G   S
           215     217     219     221     223     225     227     229     231     233

SmaI        PstI
         GCCACAGCCTGTTCACCCGGGCCATCCTGCAGAGCGGCAGCTTCAATGCCCCTTGGGCCG
721      ---------+---------+---------+---------+---------+---------+
         CGGTGTCGGACAAGTGGGCCCGGTAGGACGTCTCGCCGTCGAAGTTACGGGGAACCCGGC
          H   S   L   F   T   R   A   I   L   Q   S   G   S   F   N   A   P   W   A   V
           235     237     239     241     243     245     247     249     251     253

PstI
         TGACCAGCCTGTACGAGGCCCGGAACCGGACCCTGAACCTGGCCAAGCTGACCGGCTGCA
781      ---------+---------+---------+---------+---------+---------+
         ACTGGTCGGACATGCTCCGGGCCTTGGCCTGGGACTTGGACCGGTTCGACTGGCCGACGT
          T   S   L   Y   E   A   R   N   R   T   L   N   L   A   K   L   T   G   C   S
           255     257     259     261     263     265     267     269     271     273

GCAGAGAGAACGAGACAGAGATCATCAAGTGCCTGCGGAACAAGGACCCCCAGGAAATCC
841      ---------+---------+---------+---------+---------+---------+
         CGTCTCTCTTGCTCTGTCTCTAGTAGTTCACGGACGCCTTGTTCCTGGGGGTCCTTTAGG
          R   E   N   E   T   E   I   I   K   C   L   R   N   K   D   P   Q   E   I   L
           275     277     279     281     283     285     287     289     291     293

StuI
         TGCTGAACGAGGCCTTCGTGGTGCCCTACGGCACCCCCCTGAGCGTGAACTTCGGCCCTA
901      ---------+---------+---------+---------+---------+---------+
         ACGACTTGCTCCGGAAGCACCACGGGATGCCGTGGGGGGACTCGCACTTGAAGCCGGGAT
          L   N   E   A   F   V   V   P   Y   G   T   P   L   S   V   N   F   G   P   T
           295     297     299     301     303     305     307     309     311     313
```

Figure 1 - 3

```
        CCGTGGACGGCGACTTCCTGACCGACATGCCCGACATCCTGCTGGAACTGGGACAGTTCA
 961    ---------+---------+---------+---------+---------+---------+
        GGCACCTGCCGCTGAAGGACTGGCTGTACGGGCTGTAGGACGACCTTGACCCTGTCAAGT
         _V__D__G__D__F__L__T__D__M__P__D__I__L__L__E__L__G__Q__F__K_
          315   317   319   321   323   325   327   329   331   333

PflMI
        AGAAAACCCAGATCCTGGTGGGAGTGAACAAGGACGAGGGAACCGCCTTCCTGGTGTACG
1021    ---------+---------+---------+---------+---------+---------+
        TCTTTTGGGTCTAGGACCACCCTCACTTGTTCCTGCTCCCTTGGCGGAAGGACCACATGC
         _K__T__Q__I__L__V__G__N__K__D__E__G__T__A__F__L__V__Y__G_
          335   337   339   341   343   345   347   349   351   353

StuI
        GCGCTCCCGGCTTCAGCAAGGACAACAACAGCATCATCACCCGGAAAGAGTTCCAGGAAG
1081    ---------+---------+---------+---------+---------+---------+
        CGCGAGGGCCGAAGTCGTTCCTGTTGTTGTCGTAGTAGTGGGCCTTTCTCAAGGTCCTTC
         _A__P__G__F__S__K__D__N__N__S__I__I__T__R__K__E__F__Q__E__G_
          355   357   359   361   363   365   367   369   371   373

BglII
        GCCTGAAGATCTTCTTCCCCGGCGTGTCCGAATTTGGCAAAGAGAGCATCCTGTTCCACT
1141    ---------+---------+---------+---------+---------+---------+
        CGGACTTCTAGAAGAAGGGGCCGCACAGGCTTAAACCGTTTCTCTCGTAGGACAAGGTGA
         _L__K__I__F__F__P__G__V__S__E__F__G__K__E__S__I__L__F__H__Y_
          375   377   379   381   383   385   387   389   391   393

ACACCGACTGGGTGGACGACCAGCGGCCCGAGAATTACCGGGAAGCCCTGGGCGACGTGG
1201    ---------+---------+---------+---------+---------+---------+
        TGTGGCTGACCCACCTGCTGGTCGCCGGGCTCTTAATGGCCCTTCGGGACCCGCTGCACC
         _T__D__W__V__D__D__Q__R__P__E__N__Y__R__E__A__L__G__D__V__V_
          395   397   399   401   403   405   407   409   411   413

TGGGAGACTACAACTTCATCTGCCCTGCCCTGGAGTTCACCAAGAAATTCAGCGAGTGGG
1261    ---------+---------+---------+---------+---------+---------+
        ACCCTCTGATGTTGAAGTAGACGGGACGGGACCTCAAGTGGTTCTTTAAGTCGCTCACCC
         _G__D__Y__N__F__I__C__P__A__L__E__F__T__K__K__F__S__E__W__G_
          415   417   419   421   423   425   427   429   431   433

BstBI
        GCAACAACGCCTTCTTCTACTACTTCGAACACAGAAGCAGCAAGCTGCCCTGGCCTGAGT
1321    ---------+---------+---------+---------+---------+---------+
        CGTTGTTGCGGAAGAAGATGATGAAGCTTGTGTCTTCGTCGTTCGACGGGACCGGACTCA
         _N__N__A__F__F__Y__Y__F__E__H__R__S__S__K__L__P__W__P__E__W_
          435   437   439   441   443   445   447   449   451   453

GGATGGGCGTGATGCACGGCTACGAGATCGAGTTCGTGTTCGGCCTGCCCCTGGAACGGC
1381    ---------+---------+---------+---------+---------+---------+
        CCTACCCGCACTACGTGCCGATGCTCTAGCTCAAGCACAAGCCGGACGGGGACCTTGCCG
         _M__G__V__M__H__G__Y__E__I__E__F__V__F__G__L__P__L__E__R__R_
          455   457   459   461   463   465   467   469   471   473

GGGACAACTACACCAAGGCCGAAGAGATCCTGAGCCGGTCCATCGTGAAGAGATGGGCCA
1441    ---------+---------+---------+---------+---------+---------+
        CCCTGTTGATGTGGTTCCGGCTTCTCTAGGACTCGGCCAGGTAGCACTTCTCTACCCGGT
         _D__N__Y__T__K__A__E__E__I__L__S__R__S__I__V__K__R__W__A__N_
          475   477   479   481   483   485   487   489   491   493
```

Figure 1 - 4

```
                                                        PvuII
         ACTTCGCCAAATACGGCAACCCTAACGAGACACAGAACAACAGCACCAGCTGGCCCGTGT
1501     ---------+---------+---------+---------+---------+---------+
         TGAAGCGGTTTATGCCGTTGGGATTGCTCTGTGTCTTGTTGTCGTGGTCGACCGGGCACA
          F   A   K   Y   G   N   P   N   E   T   Q   N   N   S   T   S   W   P   V   F
           495     497     499     501     503     505     507     509     511     513

TCAAGAGCACCGAGCAGAAGTACCTGACCCTGAACACCGAGAGCACCCGGATCATGACCA
1561     ---------+---------+---------+---------+---------+---------+
         AGTTCTCGTGGCTCGTCTTCATGGACTGGGACTTGTGGCTCTCGTGGGCCTAGTACTGGT
          K   S   T   E   Q   K   Y   L   T   L   N   T   E   S   T   R   I   M   T   K
           515     517     519     521     523     525     527     529     531     533

AGCTGCGGGCTCAGCAGTGCCGGTTCTGGACCTCATTCTTCCCAAAGGTGCTGGAAATGA
1621     ---------+---------+---------+---------+---------+---------+
         TCGACGCCCGAGTCGTCACGGCCAAGACCTGGAGTAAGAAGGGTTTCCACGACCTTTACT
          L   R   A   Q   Q   C   R   F   W   T   S   F   F   P   K   V   L   E   M   T
           535     537     539     541     543     545     547     549     551     553

AgeI
         CCGGCAACATCGACGAGGCCGAGTGGGAGTGGAAGGCCGGCTTTCACCGGTGGAACAACT
1681     ---------+---------+---------+---------+---------+---------+
         GGCCGTTGTAGCTGCTCCGGCTCACCCTCACCTTCCGGCCGAAAGTGGCCACCTTGTTGA
          G   N   I   D   E   A   E   W   E   W   K   A   G   F   H   R   W   N   N   Y
           555     557     559     561     563     565     567     569     571     573

ACATGATGGACTGGAAGAACCAGTTCAACGACTACACCAGCAAGAAAGAAAGCTGCGTGG
1741     ---------+---------+---------+---------+---------+---------+
         TGTACTACCTGACCTTCTTGGTCAAGTTGCTGATGTGGTCGTTCTTTCTTTCGACGCACC
          M   M   D   W   K   N   Q   F   N   D   Y   T   S   K   K   E   S   C   V   G
           575     577     579     581     583     585     587     589     591     593

BssHII
                   BamHI  AscI
         GCCTGTGATGAGGATCCGGCGCGCC
1801     ---------+---------+-----
         CGGACACTACTCCTAGGCCGCGCGG
          L   *   *
           595     597
```

Figure 2 - 1

```
1     ATGAAGGTCCTCATCCTTGCCTGTCTGGTGGCTCTGGCCCTTGCA    AGAGAAGATGACATC
1       M  K  V  L  I  L  A  C  L  V  A  L  A  L  A      R  E  D  D  I
        --------Signal Peptide-----------------------     1'  1

13    ATAATTGCAACAAAGAATGGAAAAGTCAGAGGGATGAACTTGACAGTTTTTGGTGGCACG
5        I  I  A  T  K  N  G  K  V  R  G  M  N  L  T  V  F  G  G  T

73    GTAACAGCCTTTCTTGGAATTCCCTATGCACAGCCACCTCTTGGTAGACTTCGATTCAAA
25       V  T  A  F  L  G  I  P  Y  A  Q  P  P  L  G  R  L  R  F  K

133   AAGCCACAGTCTCTGACCAAGTGGTCTGATATTTGGAATGCCACAAAATATGCAAATTCT
45       K  P  Q  S  L  T  K  W  S  D  I  W  N  A  T  K  Y  A  N  S

193   TGCTGTCAGAACATAGATCAAAGTTTTCCAGGCTTCCATGGATCAGAGATGTGGAACCCA
65        C  C  Q  N  I  D  Q  S  F  P  G  F  H  G  S  E  M  W  N  P

253   AACACTGACCTCAGTGAAGACTGTTTATATCTAAATGTATGGATTCCAGCACCTAAACCA
85       N  T  D  L  S  E  D  C  L  Y  L  N  V  W  I  P  A  P  K  P

313   AAAAATGCCACTGTATTGATATGGATTTATGGTGGTGGTTTTCAAACTGGAACATCATCT
105      K  N  A  T  V  L  I  W  I  Y  G  G  G  F  Q  T  G  T  S  S

373   TTACATGTTTATGATGGCAAGTTTCTGGCTCGGGTTGAAAGAGTTATTGTAGTGTCAATG
125      L  H  V  Y  D  G  K  F  L  A  R  V  E  R  V  I  V  V  S  M

433   AACTATAGGGTGGGTGCCCTAGGATTCTTAGCTTTGCCAGGAAATCCTGAGGCTCCAGGG
145      N  Y  R  V  G  A  L  G  F  L  A  L  P  G  N  P  E  A  P  G

493   AACATGGGTTTATTTGATCAACAGTTGGCTCTTCAGTGGGTTCAAAAAAATATAGCAGCC
165      N  M  G  L  F  D  Q  Q  L  A  L  Q  W  V  Q  K  N  I  A  A

553   TTTGGTGGAAATCCTAAAAGTGTAACTCTCTTTGGAGAAAGTGCAGGAGCAGCTTCAGTT
185      F  G  G  N  P  K  S  V  T  L  F  G  E  S  A  G  A  A  S  V

613   AGCCTGCATTTGCTTTCTCCTGGAAGCCATTCATTGTTCACCAGAGCCATTCTGCAAAGT
205      S  L  H  L  L  S  P  G  S  H  S  L  F  T  R  A  I  L  Q  S

673   GGTTCCTTTAATGCTCCTTGGGCGGTAACATCTCTTTATGAAGCTAGGAACAGAACGTTG
225      G  S  F  N  A  P  W  A  V  T  S  L  Y  E  A  R  N  R  T  L

733   AACTTAGCTAAATTGACTGGTTGCTCTAGAGAGAATGAGACTGAAATAATCAAGTGTCTT
245      N  L  A  K  L  T  G  C  S  R  E  N  E  T  E  I  I  K  C  L

793   AGAAATAAAGATCCCCAAGAAATTCTTCTGAATGAAGCATTTGTTGTCCCCTATGGGACT
265      R  N  K  D  P  Q  E  I  L  L  N  E  A  F  V  V  P  Y  G  T

853   CCTTTGTCAGTAAACTTTGGTCCGACCGTGGATGGTGATTTTCTCACTGACATGCCAGAC
285      P  L  S  V  N  F  G  P  T  V  D  G  D  F  L  T  D  M  P  D

913   ATATTACTTGAACTTGGACAATTTAAAAAAACCCAGATTTTGGTGGGTGTTAATAAAGAT
305      I  L  L  E  L  G  Q  F  K  K  T  Q  I  L  V  G  V  N  K  D
```

Figure 2-2

```
973   GAAGGGACAGCTTTTTTAGTCTATGGTGCTCCTGGCTTCAGCAAAGATAACAATAGTATC
325    E  G  T  A  F  L  V  Y  G  A  P  G  F  S  K  D  N  N  S  I

1033  ATAACTAGAAAAGAATTTCAGGAAGGTTTAAAAATATTTTTTCCAGGAGTGAGTGAGTTT
345    I  T  R  K  E  F  Q  E  G  L  K  I  F  F  P  G  V  S  E  F

1093  GGAAAGGAATCCATCCTTTTTCATTACACAGACTGGGTAGATGATCAGAGACCTGAAAAC
365    G  K  E  S  I  L  F  H  Y  T  D  W  V  D  D  Q  R  P  E  N

1153  TACCGTGAGGCCTTGGGTGATGTTGTTGGGGATTATAATTTCATATGCCCTGCCTTGGAG
385    Y  R  E  A  L  G  D  V  V  G  D  Y  N  F  I  C  P  A  L  E

1213  TTCACCAAGAAGTTCTCAGAATGGGGAAATAATGCCTTTTTCTACTATTTTGAACACCGA
405    F  T  K  K  F  S  E  W  G  N  N  A  F  F  Y  Y  F  E  H  R

1273  TCCTCCAAACTTCCGTGGCCAGAATGGATGGGAGTGATGCATGGCTATGAAATTGAATTT
425    S  S  K  L  P  W  P  E  W  M  G  V  M  H  G  Y  E  I  E  F

1333  GTCTTTGGTTTACCTCTGGAAAGAAGAGATAATTACACAAAAGCCGAGGAAATTTTGAGT
445    V  F  G  L  P  L  E  R  R  D  N  Y  T  K  A  E  E  I  L  S

1393  AGATCCATAGTGAAACGGTGGGCAAATTTTGCAAAATATGGGAATCCAAATGAGACTCAG
465    R  S  I  V  K  R  W  A  N  F  A  K  Y  G  N  P  N  E  T  Q

1453  AACAATAGCACAAGCTGGCCTGTCTTCAAAAGCACTGAACAAAAATATCTAACCTTGAAT
485    N  N  S  T  S  W  P  V  F  K  S  T  E  Q  K  Y  L  T  L  N

1513  ACAGAGTCAACAAGAATAATGACGAAACTACGTGCTCAACAATGTCGATTCTGGACATCA
505    T  E  S  T  R  I  M  T  K  L  R  A  Q  Q  C  R  F  W  T  S

1573  TTTTTTCCAAAAGTCTTGGAAATGACAGGAAATATTGATGAAGCAGAATGGGAGTGGAAA
525    F  F  P  K  V  L  E  M  T  G  N  I  D  E  A  E  W  E  W  K

1633  GCAGGATTCCATCGCTGGAACAATTACATGATGGACTGGAAAAATCAATTTAACGATTAC
545    A  G  F  H  R  W  N  N  Y  M  M  D  W  K  N  Q  F  N  D  Y

1693  ACTAGCAAGAAAGAAAGTTGTGTGGGTCTCTAA
565    T  S  K  K  E  S  C  V  G  L  *
```

Figure 3 – 1

```
    TTAATTAAGAATTCGCCACCATGGCCTGCCCCGGCTTTCTGTGGGCCCTGGTGATCAGCA
1   ---------+---------+---------+---------+---------+---------+
    AATTAATTCTTAAGCGGTGGTACCGGACGGGGCCGAAAGACACCCGGGACCACTAGTCGT
                    M   A   C   P   G   F   L   W   A   L   V   I   S   T
                    1       3       5       7       9      11      13

CCTGTCTGGAATTTTCTATGGCCGAGGACGACATCATCATTGCCACCAAGAACGGCAAAG
61  ---------+---------+---------+---------+---------+---------+
    GGACAGACCTTAAAAGATACCGGCTCCTGCTGTAGTAGTAACGGTGGTTCTTGCCGTTTC
     C   L   E   F   S   M   A   E   D   D   I   I   I   A   T   K   N   G   K   V
        15      17      19      21      23      25      27      29      31      33

TGCGGGGCATGAACCTGACCGTGTTCGGCGGCACCGTGACCGCCTTTCTGGGCATCCCTT
121 ---------+---------+---------+---------+---------+---------+
    ACGCCCCGTACTTGGACTGGCACAAGCCGCCGTGGCACTGGCGGAAAGACCCGTAGGGAA
     R   G   M   N   L   T   V   F   G   G   T   V   T   A   F   L   G   I   P   Y
        35      37      39      41      43      45      47      49      51      53

ACGCCCAGCCCCCCCTGGGCCGGCTGAGATTCAAGAAGCCCCAGAGCCTGACCAAGTGGT
181 ---------+---------+---------+---------+---------+---------+
    TGCGGGTCGGGGGGGACCCGGCCGACTCTAAGTTCTTCGGGGTCTCGGACTGGTTCACCA
     A   Q   P   P   L   G   R   L   R   F   K   K   P   Q   S   L   T   K   W   S
        55      57      59      61      63      65      67      69      71      73

PvuII
    CCGACATCTGGAACGCCACCAAATACGCCAACAGCTGCTGCCAGAACATCGACCAGAGCT
241 ---------+---------+---------+---------+---------+---------+
    GGCTGTAGACCTTGCGGTGGTTTATGCGGTTGTCGACGACGGTCTTGTAGCTGGTCTCGA
     D   I   W   N   A   T   K   Y   A   N   S   C   C   Q   N   I   D   Q   S   F
        75      77      79      81      83      85      87      89      91      93

TCCCCGGCTTCCACGGCAGCGAGATGTGGAACCCCAACACCGACCTGAGCGAGGACTGCC
301 ---------+---------+---------+---------+---------+---------+
    AGGGGCCGAAGGTGCCGTCGCTCTACACCTTGGGGTTGTGGCTGGACTCGCTCCTGACGG
     P   G   F   H   G   S   E   M   W   N   P   N   T   D   L   S   E   D   C   L
        95      97      99     101     103     105     107     109     111     113

TGTACCTGAACGTGTGGATTCCCGCCCCTAAGCCCAAGAACGCCACCGTGCTGATCTGGA
361 ---------+---------+---------+---------+---------+---------+
    ACATGGACTTGCACACCTAAGGGCGGGGATTCGGGTTCTTGCGGTGGCACGACTAGACCT
     Y   L   N   V   W   I   P   A   P   K   P   K   N   A   T   V   L   I   W   I
       115     117     119     121     123     125     127     129     131     133

TCTACGGCGGAGGCTTCCAGACCGGCACCAGCAGCCTGCACGTGTACGACGGCAAGTTCC
421 ---------+---------+---------+---------+---------+---------+
    AGATGCCGCCTCCGAAGGTCTGGCCGTGGTCGTCGGACGTGCACATGCTGCCGTTCAAGG
     Y   G   G   F   Q   T   G   T   S   S   L   H   V   Y   D   G   K   F   L
       135     137     139     141     143     145     147     149     151     153

NarI
                                                            KasI
    TGGCCAGAGTGGAACGCGTGATCGTGGTGTCCATGAACTACAGAGTGGGCGCCCTGGGCT
481 ---------+---------+---------+---------+---------+---------+
    ACCGGTCTCACCTTGCGCACTAGCACCACAGGTACTTGATGTCTCACCCGCGGGACCCGA
     A   R   V   E   R   V   I   V   V   S   M   N   Y   R   V   G   A   L   G   F
       155     157     159     161     163     165     167     169     171     173
```

Figure 3 - 2

```
                                                                    PvuII
                                                                PflMI
        TCCTGGCTCTGCCCGGAAATCCCGAGGCCCCTGGCAACATGGGCCTGTTCGACCAGCAGC
541     ---------+---------+---------+---------+---------+---------+
        AGGACCGAGACGGGCCTTTAGGGCTCCGGGGACCGTTGTACCCGGACAAGCTGGTCGTCG
         L   A   L   P   G   N   P   E   A   P   G   N   M   G   L   F   D   Q   Q   L
         175     177     179     181     183     185     187     189     191     193

PstI
        TGGCCCTGCAGTGGGTGCAGAAGAATATCGCCGCCTTCGGCGGCAACCCCAAGAGCGTGA
601     ---------+---------+---------+---------+---------+---------+
        ACCGGGACGTCACCCACGTCTTCTTATAGCGGCGGAAGCCGCCGTTGGGGTTCTCGCACT
         A   L   Q   W   V   Q   K   N   I   A   A   F   G   G   N   P   K   S   V   T
         195     197     199     201     203     205     207     209     211     213

CCCTGTTTGGCGAGTCTGCCGGCGCTGCCAGCGTGTCCCTGCATCTGCTGAGCCCTGGCA
661     ---------+---------+---------+---------+---------+---------+
        GGGACAAACCGCTCAGACGGCCGCGACGGTCGCACAGGGACGTAGACGACTCGGGACCGT
         L   F   G   E   S   A   G   A   A   S   V   S   L   H   L   L   S   P   G   S
         215     217     219     221     223     225     227     229     231     233

SmaI         PstI
        GCCACAGCCTGTTCACCCGGGCCATCCTGCAGAGCGGCAGCTTCAATGCCCCTTGGGCCG
721     ---------+---------+---------+---------+---------+---------+
        CGGTGTCGGACAAGTGGGCCCGGTAGGACGTCTCGCCGTCGAAGTTACGGGGAACCCGGC
         H   S   L   F   T   R   A   I   L   Q   S   G   S   F   N   A   P   W   A   V
         235     237     239     241     243     245     247     249     251     253

PstI
        TGACCAGCCTGTACGAGGCCCGGAACCGGACCCTGAACCTGGCCAAGCTGACCGGCTGCA
781     ---------+---------+---------+---------+---------+---------+
        ACTGGTCGGACATGCTCCGGGCCTTGGCCTGGGACTTGGACCGGTTCGACTGGCCGACGT
         T   S   L   Y   E   A   R   N   R   T   L   N   L   A   K   L   T   G   C   S
         255     257     259     261     263     265     267     269     271     273

GCAGAGAGAACGAGACAGAGATCATCAAGTGCCTGCGGAACAAGGACCCCCAGGAAATCC
841     ---------+---------+---------+---------+---------+---------+
        CGTCTCTCTTGCTCTGTCTCTAGTAGTTCACGGACGCCTTGTTCCTGGGGGTCCTTTAGG
         R   E   N   E   T   E   I   I   K   C   L   R   N   K   D   P   Q   E   I   L
         275     277     279     281     283     285     287     289     291     293

StuI
        TGCTGAACGAGGCCTTCGTGGTGCCCTACGGCACCCCCCTGAGCGTGAACTTCGGCCCTA
901     ---------+---------+---------+---------+---------+---------+
        ACGACTTGCTCCGGAAGCACCACGGGATGCCGTGGGGGGACTCGCACTTGAAGCCGGGAT
         L   N   E   A   F   V   V   P   Y   G   T   P   L   S   V   N   F   G   P   T
         295     297     299     301     303     305     307     309     311     313

CCGTGGACGGCGACTTCCTGACCGACATGCCCGACATCCTGCTGGAACTGGGACAGTTCA
961     ---------+---------+---------+---------+---------+---------+
        GGCACCTGCCGCTGAAGGACTGGCTGTACGGGCTGTAGGACGACCTTGACCCTGTCAAGT
         V   D   G   D   F   L   T   D   M   P   D   I   L   L   E   L   G   Q   F   K
         315     317     319     321     323     325     327     329     331     333
```

Figure 3 - 3

```
          PflMI
          AGAAAACCCAGATCCTGGTGGGAGTGAACAAGGACGAGGGAACCGCCTTCCTGGTGTACG
1021      ----------+---------+---------+---------+---------+---------+
          TCTTTTGGGTCTAGGACCACCCTCACTTGTTCCTGCTCCCTTGGCGGAAGGACCACATGC
           K  T  Q  I  L  V  G  V  N  K  D  E  G  T  A  F  L  V  Y  G
           335   337   339   341   343   345   347   349   351   353

StuI
          GCGCTCCCGGCTTCAGCAAGGACAACAACAGCATCATCACCCGGAAAGAGTTCCAGGAAG
1081      ----------+---------+---------+---------+---------+---------+
          CGCGAGGGCCGAAGTCGTTCCTGTTGTTGTCGTAGTAGTGGGCCTTTCTCAAGGTCCTTC
           A  P  G  F  S  K  D  N  N  S  I  I  T  R  K  E  F  Q  E  G
           355   357   359   361   363   365   367   369   371   373

BglII
          GCCTGAAGATCTTCTTCCCCGGCGTGTCCGAATTTGGCAAAGAGAGCATCCTGTTCCACT
1141      ----------+---------+---------+---------+---------+---------+
          CGGACTTCTAGAAGAAGGGGCCGCACAGGCTTAAACCGTTTCTCTCGTAGGACAAGGTGA
           L  K  I  F  F  P  G  V  S  E  F  G  K  E  S  I  L  F  H  Y
           375   377   379   381   383   385   387   389   391   393

ACACCGACTGGGTGGACGACCAGCGGCCCGAGAATTACCGGGAAGCCCTGGGCGACGTGG
1201      ----------+---------+---------+---------+---------+---------+
          TGTGGCTGACCCACCTGCTGGTCGCCGGGCTCTTAATGGCCCTTCGGGACCCGCTGCACC
           T  D  W  V  D  D  Q  R  P  E  N  Y  R  E  A  L  G  D  V  V
           395   397   399   401   403   405   407   409   411   413

TGGGAGACTACAACTTCATCTGCCCTGCCCTGGAGTTCACCAAGAAATTCAGCGAGTGGG
1261      ----------+---------+---------+---------+---------+---------+
          ACCCTCTGATGTTGAAGTAGACGGGACGGGACCTCAAGTGGTTCTTTAAGTCGCTCACCC
           G  D  Y  N  F  I  C  P  A  L  E  F  T  K  K  F  S  E  W  G
           415   417   419   421   423   425   427   429   431   433

BstBI
          GCAACAACGCCTTCTTCTACTACTTCGAACACAGAAGCAGCAAGCTGCCCTGGCCTGAGT
1321      ----------+---------+---------+---------+---------+---------+
          CGTTGTTGCGGAAGAAGATGATGAAGCTTGTGTCTTCGTCGTTCGACGGGACCGGACTCA
           N  N  A  F  F  Y  Y  F  E  H  R  S  S  K  L  P  W  P  E  W
           435   437   439   441   443   445   447   449   451   453

GGATGGGCGTGATGCACGGCTACGAGATCGAGTTCGTGTTCGGCCTGCCCCTGGAACGGC
1381      ----------+---------+---------+---------+---------+---------+
          CCTACCCGCACTACGTGCCGATGCTCTAGCTCAAGCACAAGCCGGACGGGGACCTTGCCG
           M  G  V  M  H  G  Y  E  I  E  F  V  F  G  L  P  L  E  R  R
           455   457   459   461   463   465   467   469   471   473

GGGACAACTACACCAAGGCCGAAGAGATCCTGAGCCGGTCCATCGTGAAGAGATGGGCCA
1441      ----------+---------+---------+---------+---------+---------+
          CCCTGTTGATGTGGTTCCGGCTTCTCTAGGACTCGGCCAGGTAGCACTTCTCTACCCGGT
           D  N  Y  T  K  A  E  E  I  L  S  R  S  I  V  K  R  W  A  N
           475   477   479   481   483   485   487   489   491   493
```

Figure 3 - 4

```
                                                            PvuII
       ACTTCGCCAAATACGGCAACCCTAACGAGACACAGAACAACAGCACCAGCTGGCCCGTGT
1501   ---------+---------+---------+---------+---------+---------+
       TGAAGCGGTTTATGCCGTTGGGATTGCTCTGTGTCTTGTTGTCGTGGTCGACCGGGCACA
         F   A   K   Y   G   N   P   N   E   T   Q   N   N   S   T   S   W   P   V   F
        495     497     499     501     503     505     507     509     511     513

TCAAGAGCACCGAGCAGAAGTACCTGACCCTGAACACCGAGAGCACCCGGATCATGACCA
1561   ---------+---------+---------+---------+---------+---------+
       AGTTCTCGTGGCTCGTCTTCATGGACTGGGACTTGTGGCTCTCGTGGGCCTAGTACTGGT
         K   S   T   E   Q   K   Y   L   T   L   N   T   E   S   T   R   I   M   T   K
        515     517     519     521     523     525     527     529     531     533

AGCTGCGGGCTCAGCAGTGCCGGTTCTGGACCTCATTCTTCCCAAAGGTGCTGGAAATGA
1621   ---------+---------+---------+---------+---------+---------+
       TCGACGCCCGAGTCGTCACGGCCAAGACCTGGAGTAAGAAGGGTTTCCACGACCTTTACT
         L   R   A   Q   Q   C   R   F   W   T   S   F   F   P   K   V   L   E   M   T
        535     537     539     541     543     545     547     549     551     553

BssHII
                                                     BamHI    AscI
       CCGGCAACATCGACGAGGCCGAGTGGGAGTGGTGATGAGGATCCGGCGCGCC
1681   ---------+---------+---------+---------+---------+--
       GGCCGTTGTAGCTGCTCCGGCTCACCCTCACCACTACTCCTAGGCCGCGCGG
         G   N   I   D   E   A   E   W   E   W   *   *
        555     557     559     561     563     565
```

SEQUENCE LISTING

```
<160> NUMBER OF SEQ ID NOS: 11

<210> SEQ ID NO 1
<211> LENGTH: 1825
<212> TYPE: DNA
<213> ORGANISM: Artificial
<220> FEATURE:
<223> OTHER INFORMATION: Codon Optimized Polynucleotide encoding human
      BChE

<400> SEQUENCE: 1
ttaattaaga attcgccacc atggcctgcc ccggctttct gtgggccctg gtgatcagca      60
cctgtctgga attttctatg gccgaggacg acatcatcat tgccaccaag aacggcaaag     120
tgcggggcat gaacctgacc gtgttcggcg gcaccgtgac cgcttttctg ggcatccctt     180
acgcccagcc cccccctgggc cggctgagat tcaagaagcc ccagagcctg accaagtggt    240
ccgacatctg gaacgccacc aaatacgcca acagctgctg ccagaacatc gaccagagct     300
tccccggctt ccacggcagc gagatgtgga accccaacac cgacctgagc gaggactgcc     360
tgtacctgaa cgtgtggatt cccgccccta agcccaagaa cgccaccgtg ctgatctgga     420
tctacggcgg aggcttccag accggcacca gcagcctgca cgtgtacgac ggcaagttcc     480
```

```
tggccagagt ggaacgcgtg atcgtggtgt ccatgaacta cagagtgggc gccctgggct      540
tcctggctct gcccggaaat cccgaggccc ctggcaacat gggcctgttc gaccagcagc      600
tggccctgca gtgggtgcag aagaatatcg ccgccttcgg cggcaacccc aagagcgtga      660
ccctgtttgg cgagtctgcc ggcgctgcca gcgtgtccct gcatctgctg agccctggca      720
gccacagcct gttcacccgg gccatcctgc agagcggcag cttcaatgcc ccttgggccg      780
tgaccagcct gtacgaggcc cggaaccgga ccctgaacct ggccaagctg accggctgca      840
gcagagagaa cgagacagag atcatcaagt gcctgcggaa caaggacccc caggaaatcc      900
tgctgaacga ggccttcgtg gtgccctacg gcaccccccct gagcgtgaac ttcggcccta      960
ccgtggacgg cgacttcctg accgacatgc cgacatcct gctggaactg gacagttca     1020 agaaaaccca gatcctggtg ggagtgaaca aggacgaggg aaccgccttc ctggtgtacg     1080
gcgctcccgg cttcagcaag gacaacaaca gcatcatcac ccggaaagag ttccaggaag     1140
gcctgaagat cttcttcccc ggcgtgtccg aatttggcaa agagagcatc ctgttccact     1200
acaccgactg ggtggacgac cagcggcccg agaattaccg ggaagccctg ggcgacgtgg     1260
tgggagacta caacttcatc tgccctgccc tggagttcac caagaaattc agcgagtggg     1320
gcaacaacgc cttcttctac tacttcgaac acagaagcag caagctgccc tggcctgagt     1380
ggatgggcgt gatgcacggc tacgagatcg agttcgtgtt cggcctgccc ctggaacggc     1440
gggacaacta caccaaggcc gaagagatcc tgagccggtc catcgtgaag agatgggcca     1500
acttcgccaa atacgcgaac cctaacgaga cacagaacaa cagcaccagc tggcccgtgt     1560
tcaagagcac cgagcagaag tacctgaccc tgaacaccga gagcacccgg atcatgacca     1620
agctgcgggt cagcagtgc cggttctgga cctcattctt cccaaaggtg ctggaaatga     1680
ccggcaacat cgacgaggcc gagtgggagt ggaaggccgg ctttcaccgg tggaacaact     1740
acatgatgga ctggaagaac cagttcaacg actacaccag caagaaagaa agctgcgtgg     1800
gcctgtgatg aggatccggc gcgcc                                          1825
```

<210> SEQ ID NO 2
<211> LENGTH: 595
<212> TYPE: PRT
<213> ORGANISM: Homo sapiens

<400> SEQUENCE: 2

```
Met Ala Cys Pro Gly Phe Leu Trp Ala Leu Val Ile Ser Thr Cys Leu
1               5                   10                  15

Glu Phe Ser Met Ala Glu Asp Asp Ile Ile Ile Ala Thr Lys Asn Gly
            20                  25                  30

Lys Val Arg Gly Met Asn Leu Thr Val Phe Gly Gly Thr Val Thr Ala
        35                  40                  45

Phe Leu Gly Ile Pro Tyr Ala Gln Pro Pro Leu Gly Arg Leu Arg Phe
    50                  55                  60

Lys Lys Pro Gln Ser Leu Thr Lys Trp Ser Asp Ile Trp Asn Ala Thr
65                  70                  75                  80

Lys Tyr Ala Asn Ser Cys Cys Gln Asn Ile Asp Gln Ser Phe Pro Gly
                85                  90                  95

Phe His Gly Ser Glu Met Trp Asn Pro Asn Thr Asp Leu Ser Glu Asp
            100                 105                 110

Cys Leu Tyr Leu Asn Val Trp Ile Pro Ala Pro Lys Pro Lys Asn Ala
        115                 120                 125

Thr Val Leu Ile Trp Ile Tyr Gly Gly Gly Phe Gln Thr Gly Thr Ser
```

-continued

```
                130                 135                 140
Ser Leu His Val Tyr Asp Gly Lys Phe Leu Ala Arg Val Glu Arg Val
145                 150                 155                 160

Ile Val Val Ser Met Asn Tyr Arg Val Gly Ala Leu Gly Phe Leu Ala
                165                 170                 175

Leu Pro Gly Asn Pro Glu Ala Pro Gly Asn Met Gly Leu Phe Asp Gln
                180                 185                 190

Gln Leu Ala Leu Gln Trp Val Gln Lys Asn Ile Ala Ala Phe Gly Gly
                195                 200                 205

Asn Pro Lys Ser Val Thr Leu Phe Gly Glu Ser Ala Gly Ala Ala Ser
210                 215                 220

Val Ser Leu His Leu Leu Ser Pro Gly Ser His Ser Leu Phe Thr Arg
225                 230                 235                 240

Ala Ile Leu Gln Ser Gly Ser Phe Asn Ala Pro Trp Ala Val Thr Ser
                245                 250                 255

Leu Tyr Glu Ala Arg Asn Arg Thr Leu Asn Leu Ala Lys Leu Thr Gly
                260                 265                 270

Cys Ser Arg Glu Asn Glu Thr Glu Ile Ile Lys Cys Leu Arg Asn Lys
                275                 280                 285

Asp Pro Gln Glu Ile Leu Leu Asn Glu Ala Phe Val Val Pro Tyr Gly
                290                 295                 300

Thr Pro Leu Ser Val Asn Phe Gly Pro Thr Val Asp Gly Asp Phe Leu
305                 310                 315                 320

Thr Asp Met Pro Asp Ile Leu Leu Glu Leu Gly Gln Phe Lys Lys Thr
                325                 330                 335

Gln Ile Leu Val Gly Val Asn Lys Asp Glu Gly Thr Ala Phe Leu Val
                340                 345                 350

Tyr Gly Ala Pro Gly Phe Ser Lys Asp Asn Asn Ser Ile Ile Thr Arg
                355                 360                 365

Lys Glu Phe Gln Glu Gly Leu Lys Ile Phe Phe Pro Gly Val Ser Glu
                370                 375                 380

Phe Gly Lys Glu Ser Ile Leu Phe His Tyr Thr Asp Trp Val Asp Asp
385                 390                 395                 400

Gln Arg Pro Glu Asn Tyr Arg Glu Ala Leu Gly Asp Val Val Gly Asp
                405                 410                 415

Tyr Asn Phe Ile Cys Pro Ala Leu Glu Phe Thr Lys Lys Phe Ser Glu
                420                 425                 430

Trp Gly Asn Asn Ala Phe Phe Tyr Tyr Phe Glu His Arg Ser Ser Lys
                435                 440                 445

Leu Pro Trp Pro Glu Trp Met Gly Val Met His Gly Tyr Glu Ile Glu
450                 455                 460

Phe Val Phe Gly Leu Pro Leu Glu Arg Arg Asp Asn Tyr Thr Lys Ala
465                 470                 475                 480

Glu Glu Ile Leu Ser Arg Ser Ile Val Lys Arg Trp Ala Asn Phe Ala
                485                 490                 495

Lys Tyr Gly Asn Pro Asn Glu Thr Gln Asn Asn Ser Thr Ser Trp Pro
                500                 505                 510

Val Phe Lys Ser Thr Glu Gln Lys Tyr Leu Thr Leu Asn Thr Glu Ser
                515                 520                 525

Thr Arg Ile Met Thr Lys Leu Arg Ala Gln Gln Cys Arg Phe Trp Thr
                530                 535                 540

Ser Phe Phe Pro Lys Val Leu Glu Met Thr Gly Asn Ile Asp Glu Ala
545                 550                 555                 560
```

```
Glu Trp Glu Trp Lys Ala Gly Phe His Arg Trp Asn Asn Tyr Met Met
                565                 570                 575

Asp Trp Lys Asn Gln Phe Asn Asp Tyr Thr Ser Lys Lys Glu Ser Cys
        580                 585                 590

Val Gly Leu
        595

<210> SEQ ID NO 3
<211> LENGTH: 1732
<212> TYPE: DNA
<213> ORGANISM: Artificial
<220> FEATURE:
<223> OTHER INFORMATION: Codon Optimized Polynucleotide encoding
      truncated human BChE

<400> SEQUENCE: 3
ttaattaaga attcgccacc atggcctgcc ccggcttttct gtgggccctg gtgatcagca      60
cctgtctgga attttctatg ccgaggacg acatcatcat tgccaccaag aacggcaaag     120
tgcggggcat gaacctgacc gtgttcggcg gcaccgtgac cgcctttctg ggcatccctt     180
acgcccagcc cccctgggc cggctgagat tcaagaagcc cagagcctg accaagtggt     240 ccgacatctg gaacgccacc aaatacgcca acagctgctg ccagaacatc gaccagagct     300 tcccccggctt ccacggcagc gagatgtgga accccaacac cgacctgagc gaggactgcc     360
tgtacctgaa cgtgtggatt cccgccccta gcccaagaa cgccaccgtg ctgatctgga     420
tctacggcgg aggcttccag accggcacca gcagcctgca cgtgtacgac ggcaagttcc     480
tggccagagt ggaacgcgtg atcgtggtgt ccatgaacta cagagtgggc gccctgggct     540
tcctggctct gcccggaaat cccgaggccc tggcaacat gggcctgttc gaccagcagc     600
tggccctgca gtgggtgcag aagaatatcg ccgccttcgg cggcaacccc aagagcgtga     660
ccctgtttgg cgagtctgcc ggcgctgcca gcgtgtccct gcatctgctg agccctggca     720
gccacagcct gttcacccgg gccatcctgc agagcggcag cttcaatgcc ccttgggccg     780
tgaccagcct gtacgaggcc cggaaccgga ccctgaacct ggccaagctg accggctgca     840
gcagagagaa cgagacagag atcatcaagt gcctgcggaa caggaccccc aggaaatcc     900 tgctgaacga ggccttcgtg gtgccctacg gcacccccct gagcgtgaac ttcggcccta     960
ccgtggacgc cgacttcctg accgacatgc ccgacatcct gctggaactg ggacagttca    1020 agaaaacca gatcctggtg ggagtgaaca aggacgaggg aaccgccttc ctggtgtacg    1080
gcgctcccgg cttcagcaag acaacaaca gcatcatcac ccggaaagag ttccaggaag    1140
gcctgaagat cttcttcccc ggcgtgtccg aatttggcaa agagagcatc ctgttccact    1200
acaccgactg ggtggacgac cagcggcccg agaattaccg ggaagccctg ggcgacgtgg    1260
tgggagacta caacttcatc tgccctgccc tggagttcac caagaaattc agcgagtggg    1320
gcaacaacgc cttcttctac tacttcgaac acagaagcag caagctgccc tggcctgagt    1380
ggatgggcgt gatgcacggc tacgagatcg agttcgtgtt cggcctgccc ctggaacggc    1440
gggacaacta caccaaggcc gaagagatcc tgagccggtc catcgtgaag agatgggcca    1500
acttcgccaa atacggcaac cctaacgaga cacagaacaa cagcaccagc tggcccgtgt    1560
tcaagagcac cgagcagaag tacctgaccc tgaacaccga gagcacccgg atcatgacca    1620
agctgcgggc tcagcagtgc cggttctgga cctcattctt cccaaaggtg ctggaaatga    1680
ccggcaacat cgacgaggcc gagtgggagt ggtgatgagg atccggcgcg cc            1732

<210> SEQ ID NO 4
```

```
<211> LENGTH: 564
<212> TYPE: PRT
<213> ORGANISM: Artificial
<220> FEATURE:
<223> OTHER INFORMATION: Truncated human BChE Polypeptide

<400> SEQUENCE: 4
```

| | | | | | | | | | | | | | | |
|---|---|---|---|---|---|---|---|---|---|---|---|---|---|---|
| Met | Ala | Cys | Pro | Gly | Phe | Leu | Trp | Ala | Leu | Val | Ile | Ser | Thr | Cys | Leu |
| 1 | | | | 5 | | | | | 10 | | | | | 15 | |

| Glu | Phe | Ser | Met | Ala | Glu | Asp | Ile | Ile | Ile | Ala | Thr | Lys | Asn | Gly |
|---|---|---|---|---|---|---|---|---|---|---|---|---|---|---|
| | | | 20 | | | | | 25 | | | | | 30 | |

Lys Val Arg Gly Met Asn Leu Thr Val Phe Gly Gly Thr Val Thr Ala
            35                  40                  45

Phe Leu Gly Ile Pro Tyr Ala Gln Pro Pro Leu Gly Arg Leu Arg Phe
 50                  55                  60

Lys Lys Pro Gln Ser Leu Thr Lys Trp Ser Asp Ile Trp Asn Ala Thr
65                  70                  75                  80

Lys Tyr Ala Asn Ser Cys Cys Gln Asn Ile Asp Gln Ser Phe Pro Gly
                85                  90                  95

Phe His Gly Ser Glu Met Trp Asn Pro Asn Thr Asp Leu Ser Glu Asp
                100                 105                 110

Cys Leu Tyr Leu Asn Val Trp Ile Pro Ala Pro Lys Pro Lys Asn Ala
            115                 120                 125

Thr Val Leu Ile Trp Ile Tyr Gly Gly Gly Phe Gln Thr Gly Thr Ser
    130                 135                 140

Ser Leu His Val Tyr Asp Gly Lys Phe Leu Ala Arg Val Glu Arg Val
145                 150                 155                 160

Ile Val Val Ser Met Asn Tyr Arg Val Gly Ala Leu Gly Phe Leu Ala
                165                 170                 175

Leu Pro Gly Asn Pro Glu Ala Pro Gly Asn Met Gly Leu Phe Asp Gln
            180                 185                 190

Gln Leu Ala Leu Gln Trp Val Gln Lys Asn Ile Ala Ala Phe Gly Gly
        195                 200                 205

Asn Pro Lys Ser Val Thr Leu Phe Gly Glu Ser Ala Gly Ala Ala Ser
210                 215                 220

Val Ser Leu His Leu Leu Ser Pro Gly Ser His Ser Leu Phe Thr Arg
225                 230                 235                 240

Ala Ile Leu Gln Ser Gly Ser Phe Asn Ala Pro Trp Ala Val Thr Ser
                245                 250                 255

Leu Tyr Glu Ala Arg Asn Arg Thr Leu Asn Leu Ala Lys Leu Thr Gly
            260                 265                 270

Cys Ser Arg Glu Asn Glu Thr Glu Ile Ile Lys Cys Leu Arg Asn Lys
        275                 280                 285

Asp Pro Gln Glu Ile Leu Leu Asn Glu Ala Phe Val Val Pro Tyr Gly
290                 295                 300

Thr Pro Leu Ser Val Asn Phe Gly Pro Thr Val Asp Gly Asp Phe Leu
305                 310                 315                 320

Thr Asp Met Pro Asp Ile Leu Leu Glu Leu Gly Gln Phe Lys Lys Thr
                325                 330                 335

Gln Ile Leu Val Gly Val Asn Lys Asp Glu Gly Thr Ala Phe Leu Val
            340                 345                 350

Tyr Gly Ala Pro Gly Phe Ser Lys Asp Asn Asn Ser Ile Ile Thr Arg
        355                 360                 365

Lys Glu Phe Gln Glu Gly Leu Lys Ile Phe Phe Pro Gly Val Ser Glu
    370                 375                 380

```
Phe Gly Lys Glu Ser Ile Leu Phe His Tyr Thr Asp Trp Val Asp Asp
385                 390                 395                 400

Gln Arg Pro Glu Asn Tyr Arg Glu Ala Leu Gly Asp Val Val Gly Asp
            405                 410                 415

Tyr Asn Phe Ile Cys Pro Ala Leu Glu Phe Thr Lys Lys Phe Ser Glu
        420                 425                 430

Trp Gly Asn Asn Ala Phe Phe Tyr Tyr Phe Glu His Arg Ser Ser Lys
            435                 440                 445

Leu Pro Trp Pro Glu Trp Met Gly Val Met His Gly Tyr Glu Ile Glu
        450                 455                 460

Phe Val Phe Gly Leu Pro Leu Glu Arg Arg Asp Asn Tyr Thr Lys Ala
465                 470                 475                 480

Glu Glu Ile Leu Ser Arg Ser Ile Val Lys Arg Trp Ala Asn Phe Ala
                485                 490                 495

Lys Tyr Gly Asn Pro Asn Glu Thr Gln Asn Asn Ser Thr Ser Trp Pro
            500                 505                 510

Val Phe Lys Ser Thr Glu Gln Lys Tyr Leu Thr Leu Asn Thr Glu Ser
        515                 520                 525

Thr Arg Ile Met Thr Lys Leu Arg Ala Gln Gln Cys Arg Phe Trp Thr
    530                 535                 540

Ser Phe Phe Pro Lys Val Leu Glu Met Thr Gly Asn Ile Asp Glu Ala
545                 550                 555                 560

Glu Trp Glu Trp

<210> SEQ ID NO 5
<211> LENGTH: 1773
<212> TYPE: DNA
<213> ORGANISM: Artificial
<220> FEATURE:
<223> OTHER INFORMATION: Polynucleotide encoding fusion of human BChE
      Polypeptide with goat signal sequence

<400> SEQUENCE: 5
atgaaggtcc tcatccttgc ctgtctggtg gctctggccc ttgcaagaga agatgacatc      60
ataattgcaa caagaatgg aaaagtcaga gggatgaact tgacagtttt tggtggcacg     120
gtaacagcct ttcttggaat tccctatgca cagccacctc ttggtagact tcgattcaaa     180
aagccacagt ctctgaccaa gtggtctgat atttggaatg ccacaaaata tgcaaattct     240
tgctgtcaga acatagatca aagttttcca ggcttccatg gatcagagat gtggaaccca     300
aacactgacc tcagtgaaga ctgtttatat ctaaatgtat ggattccagc acctaaacca     360
aaaaatgcca ctgtattgat atggatttat ggtggtggtt tcaaactgg aacatcatct     420 ttacatgttt atgatggcaa gtttctggct cgggttgaaa gagttattgt agtgtcaatg     480
aactataggg tgggtgccct aggattctta gctttgccag gaaatcctga ggctccaggg     540
aacatggggt tatttgatca acagttggct cttcagtggg ttcaaaaaaa tatagcagcc     600
tttggtggaa atcctaaaag tgtaactctc tttggagaaa gtgcaggagc agcttcagtt     660
agcctgcatt tgctttctcc tggaagccat tcattgttca ccagagcat tctgcaaagt     720 ggttccttta atgctccttg gcggtaaca tctctttatg aagctaggaa cagaacgttg     780
aacttagcta aattgactgg ttgctctaga gagaatgaga ctgaaataat caagtgtctt     840
agaaataaag atccccaaga aattcttctg aatgaagcat tgttgtccc ctatgggact     900 cctttgtcag taaactttgg tccgaccgtg gatggtgatt ttctcactga catgccagac     960
atattacttg aacttggaca atttaaaaaa acccagattt tggtgggtgt taataaagat    1020
```

```
                                                          -continued
gaagggacag ctttttagt ctatggtgct cctggcttca gcaaagataa caatagtatc      1080
ataactagaa aagaatttca ggaaggttta aaatatttt ttccaggagt gagtgagttt      1140
ggaaaggaat ccatccttt tcattacaca gactgggtag atgatcagag acctgaaaac     1200
taccgtgagg ccttgggtga tgttgttggg gattataatt tcatatgccc tgccttggag    1260
ttcaccaaga agttctcaga atggggaaat aatgcctttt tctactattt tgaacaccga    1320
tcctccaaac ttccgtggcc agaatggatg ggagtgatgc atggctatga aattgaattt   1380
gtctttggtt tacctctgga agaagagat aattacacaa aagccgagga aattttgagt    1440
agatccatag tgaaacggtg ggcaaatttt gcaaaatatg gaatccaaa tgagactcag    1500 aacaatagca caagctggcc tgtcttcaaa agcactgaac aaaaatatct aaccttgaat   1560
acagagtcaa caagaataat gacgaaacta cgtgctcaac aatgtcgatt ctggacatca   1620
ttttttccaa aagtcttgga aatgacagga atattgatg aagcagaatg ggagtggaaa   1680
gcaggattcc atcgctggaa caattacatg atggactgga aaatcaatt taacgattac   1740 actagcaaga aagaaagttg tgtgggtctc taa                                 1773

<210> SEQ ID NO 6
<211> LENGTH: 590
<212> TYPE: PRT
<213> ORGANISM: Artificial
<220> FEATURE:
<223> OTHER INFORMATION: Fusion of human BChE Polypeptide with goat
      signal sequence

<400> SEQUENCE: 6

Met Lys Val Leu Ile Leu Ala Cys Leu Val Ala Leu Ala Leu Ala Arg
1               5                  10                  15

Glu Asp Asp Ile Ile Ile Ala Thr Lys Asn Gly Lys Val Arg Gly Met
            20                  25                  30

Asn Leu Thr Val Phe Gly Gly Thr Val Thr Ala Phe Leu Gly Ile Pro
        35                  40                  45

Tyr Ala Gln Pro Pro Leu Gly Arg Leu Arg Phe Lys Lys Pro Gln Ser
    50                  55                  60

Leu Thr Lys Trp Ser Asp Ile Trp Asn Ala Thr Lys Tyr Ala Asn Ser
65                  70                  75                  80

Cys Cys Gln Asn Ile Asp Gln Ser Phe Pro Gly Phe His Gly Ser Glu
                85                  90                  95

Met Trp Asn Pro Asn Thr Asp Leu Ser Glu Asp Cys Leu Tyr Leu Asn
            100                 105                 110

Val Trp Ile Pro Ala Pro Lys Pro Lys Asn Ala Thr Val Leu Ile Trp
        115                 120                 125

Ile Tyr Gly Gly Gly Phe Gln Thr Gly Thr Ser Ser Leu His Val Tyr
    130                 135                 140

Asp Gly Lys Phe Leu Ala Arg Val Glu Arg Val Ile Val Val Ser Met
145                 150                 155                 160

Asn Tyr Arg Val Gly Ala Leu Gly Phe Leu Ala Leu Pro Gly Asn Pro
                165                 170                 175

Glu Ala Pro Gly Asn Met Gly Leu Phe Asp Gln Gln Leu Ala Leu Gln
            180                 185                 190

Trp Val Gln Lys Asn Ile Ala Ala Phe Gly Gly Asn Pro Lys Ser Val
        195                 200                 205

Thr Leu Phe Gly Glu Ser Ala Gly Ala Ala Ser Val Ser Leu His Leu
    210                 215                 220

Leu Ser Pro Gly Ser His Ser Leu Phe Thr Arg Ala Ile Leu Gln Ser
```

```
                225                 230                 235                 240
Gly Ser Phe Asn Ala Pro Trp Ala Val Thr Ser Leu Tyr Glu Ala Arg
                245                 250                 255
Asn Arg Thr Leu Asn Leu Ala Lys Leu Thr Gly Cys Ser Arg Glu Asn
                260                 265                 270
Glu Thr Glu Ile Ile Lys Cys Leu Arg Asn Lys Asp Pro Gln Glu Ile
                275                 280                 285
Leu Leu Asn Glu Ala Phe Val Val Pro Tyr Gly Thr Pro Leu Ser Val
                290                 295                 300
Asn Phe Gly Pro Thr Val Asp Gly Asp Phe Leu Thr Asp Met Pro Asp
305                 310                 315                 320
Ile Leu Glu Leu Gly Gln Phe Lys Lys Thr Gln Ile Leu Val Gly
                325                 330                 335
Val Asn Lys Asp Glu Gly Thr Ala Phe Leu Val Tyr Gly Ala Pro Gly
                340                 345                 350
Phe Ser Lys Asp Asn Asn Ser Ile Ile Thr Arg Lys Glu Phe Gln Glu
                355                 360                 365
Gly Leu Lys Ile Phe Phe Pro Gly Val Ser Glu Phe Gly Lys Glu Ser
                370                 375                 380
Ile Leu Phe His Tyr Thr Asp Trp Val Asp Asp Gln Arg Pro Glu Asn
385                 390                 395                 400
Tyr Arg Glu Ala Leu Gly Asp Val Val Gly Asp Tyr Asn Phe Ile Cys
                405                 410                 415
Pro Ala Leu Glu Phe Thr Lys Lys Phe Ser Glu Trp Gly Asn Asn Ala
                420                 425                 430
Phe Phe Tyr Tyr Phe Glu His Arg Ser Ser Lys Leu Pro Trp Pro Glu
                435                 440                 445
Trp Met Gly Val Met His Gly Tyr Glu Ile Glu Phe Val Phe Gly Leu
                450                 455                 460
Pro Leu Glu Arg Arg Asp Asn Tyr Thr Lys Ala Glu Glu Ile Leu Ser
465                 470                 475                 480
Arg Ser Ile Val Lys Arg Trp Ala Asn Phe Ala Lys Tyr Gly Asn Pro
                485                 490                 495
Asn Glu Thr Gln Asn Asn Ser Thr Ser Trp Pro Val Phe Lys Ser Thr
                500                 505                 510
Glu Gln Lys Tyr Leu Thr Leu Asn Thr Glu Ser Thr Arg Ile Met Thr
                515                 520                 525
Lys Leu Arg Ala Gln Gln Cys Arg Phe Trp Thr Ser Phe Phe Pro Lys
                530                 535                 540
Val Leu Glu Met Thr Gly Asn Ile Asp Glu Ala Glu Trp Glu Trp Lys
545                 550                 555                 560
Ala Gly Phe His Arg Trp Asn Asn Tyr Met Met Asp Trp Lys Asn Gln
                565                 570                 575
Phe Asn Asp Tyr Thr Ser Lys Lys Glu Ser Cys Val Gly Leu
                580                 585                 590

<210> SEQ ID NO 7
<211> LENGTH: 31
<212> TYPE: PRT
<213> ORGANISM: Artificial
<220> FEATURE:
<223> OTHER INFORMATION: Oligopeptide from amino acids 565-595 of SEQ
      ID NO: 2

<400> SEQUENCE: 7

Lys Ala Gly Phe His Arg Trp Asn Asn Tyr Met Met Asp Trp Lys Asn
```

```
              1               5                    10                       15
    Gln Phe Asn Asp Tyr Thr Ser Lys Lys Glu Ser Cys Val Gly Leu
                          20                   25                  30
```

<210> SEQ ID NO 8
<211> LENGTH: 8
<212> TYPE: DNA
<213> ORGANISM: Artificial
<220> FEATURE:
<223> OTHER INFORMATION: Chi sequence

<400> SEQUENCE: 8 gctggtgg                                                              8

<210> SEQ ID NO 9
<211> LENGTH: 10
<212> TYPE: RNA
<213> ORGANISM: Artificial
<220> FEATURE:
<223> OTHER INFORMATION: Kozak sequence

<400> SEQUENCE: 9
accaccaugg                                                           10

<210> SEQ ID NO 10
<211> LENGTH: 10
<212> TYPE: RNA
<213> ORGANISM: Artificial
<220> FEATURE:
<223> OTHER INFORMATION: Kozak sequence

<400> SEQUENCE: 10
gccaccaugg                                                           10

<210> SEQ ID NO 11
<211> LENGTH: 7
<212> TYPE: DNA
<213> ORGANISM: Artificial
<220> FEATURE:
<223> OTHER INFORMATION: Transcription initiation site

<400> SEQUENCE: 11 tataaaa                                                               7

US 8,729,245 B2

RECOMBINANT BUTYRYLCHOLINESTERASES AND TRUNCATES THEREOF

This application claims priority of U.S. provisional Application 61/284,444, filed 21 Dec. 2009, the disclosure of which is herein incorporated by reference in its entirety.

FIELD OF THE INVENTION

The present invention provides methods for the production of recombinant butyrylcholinesterases using polynucleotides codon-optimized for expression in mammalian, especially human, cells, including truncates thereof.

BACKGROUND OF THE INVENTION

The general term cholinesterase (ChE) refers to a family of enzymes involved in nerve impulse transmission. Cholinesterase-inhibiting substances such as organophosphate compounds or carbamate insecticides or drugs prevent the breakdown of acetylcholine, resulting in a buildup of acetylcholine, thereby causing hyperactivity of the nervous system. When humans breathe or are otherwise exposed to these compounds, which has led to the development of these compounds as "nerve gases" or chemical warfare agents.

Those enzymes which preferentially hydrolyze other types of esters such as butyrylcholine, and whose enzymatic activity is sensitive to the chemical inhibitor tetraisopropylpyrophosphoramide (also known as iso-OMPA), are called butyrylcholinesterases (BChE, EC 3.1.1.8).

Butyrylcholinesterase (BChE), also known as plasma, serum, benzoyl, false, or Type II ChE, has more than eleven isoenzyme variants and preferentially uses butyrylcholine and benzoylcholine as in vitro substrates. BChE is found in mammalian blood plasma, liver, pancreas, intestinal mucosa, the white matter of the central nervous system, smooth muscle, and heart. BChE is sometimes referred to as serum cholinesterase as opposed to red cell cholinesterase (AChE).

The use of cholinesterases as pre-treatment drugs has been successfully demonstrated in animals, including non-human primates. For example, pretreatment of rhesus monkeys with fetal bovine serum-derived AChE or horse serum-derived BChE protected them against a challenge of two to five times the LD50 of pinacolyl methylphosphonofluoridate (soman), a highly toxic organophophate compound used as a war-gas [Broomfield, et al. J. Pharmacol. Exp. Ther. (1991) 259:633-638; Wolfe, et al. Toxicol Appl Pharmacol (1992) 117(2):189-193]. In addition to preventing lethality, the pretreatment prevented behavioral incapacitation after the soman challenge, as measured by the serial probe recognition task or the equilibrium platform performance task. Administration of sufficient exogenous human BChE can protect mice, rats, and monkeys from multiple lethal-dose organophosphate intoxication [see for example Raveh, et al. Biochemical Pharmacology (1993) 42:2465-2474; Raveh, et al. Toxicol. Appl. Pharmacol. (1997) 145:43-53; Alton, et al. Toxicol. Sci. (1998) 43:121-128]. Purified human BChE has been used to treat organophosphate poisoning in humans, with no significant adverse immunological or psychological effects (Cascio, et al. Minerva Anestesiol (1998) 54:337).

In addition to its efficacy in hydrolyzing organophosphate toxins, there is strong evidence that BChE is the major detoxifying enzyme of cocaine [Xie, et al. Molec. Pharmacol. (1999) 55:83-91]. Cocaine is metabolized by three major routes: hydrolysis by BChE to form ecgonine methyl ester, N-demethylation from norcocaine, and non-enzymatic hydrolysis to form benzoylcholine. Studies have shown a direct correlation between low BChE levels and episodes of life-threatening cocaine toxicity. A recent study has confirmed that a decrease of cocaine half-life in vitro correlated with the addition of purified human BChE.

In view of the significant pharmaceutical potential of ChE enzymes, research has focused on development of recombinant methods to produce them. Recombinant enzymes, as opposed to those derived from plasma, have a much lower risk of transmission of infectious agents, including viruses such as hepatitis C and HIV.

The cDNA sequences have been cloned for both human AChE (see U.S. Pat. No. 5,595,903) and human BChE [see U.S. Pat. No. 5,215,909 to Soreq; Prody, et al. Proc. Natl. Acad. Sci. USA (1987) 84:3555-3559; McTiernan, et al. Proc. Natl. Acad. Sci USA (1987) 84:6682-6686]. The amino acid sequence of wild-type human BChE, as well as of several BChE variants with single amino acid changes, is set forth in U.S. Pat. No. 6,001,625.

Notably, none of the recombinant expression systems reported to date have the ability to produce BChE in quantities sufficient to allow development of the enzyme as a drug to treat such conditions as organophosphate poisoning, post-surgical apnea, or cocaine intoxication. However, an additional problem is longevity. Thus, the longer the BChE remains in the system of a person treated, the longer it is available for detoxification. Such lifespan is referred to as the "mean residence time" (MRT) in the system.

The current state of art for BChE is directed to making the tetramer form because it is the "native form" and is thus considered to be more stable with a longer "mean residence time" (MRT). However, due to the very large size of the tetramer, it is difficult to prepare. In addition, such preparation usually results in a mixture of tetramer, dimer and monomer forms with low yield. Such preparation has proven both very cumbersome and very expensive to purify and characterize. As a result, it is probably too expensive to make as a useful therapeutic product. In view of the foregoing, more powerful methods of producing BChE are needed.

In sum, the current obstacles in the manufacture of the native BChE molecule as a bioscavenger product which are: 1) low yield, 2) complex manufacturing process (milk), 3) short half-life (thus requiring pegylation), 4) highly heterogeneous product (difficult to characterize and obtain FDA approval) and 5) high cost of the product.

The present invention addresses at least some of these problems by providing inter alia a truncated monomeric form of BChE. While the the monomer form is just as active as the tetrameric form, it has been considered to be less stable (i.e., have a lower "MRT") than the tetramer. This may be because the protein made is not properly glycosylated and/or sialylated. Applicants have identified a cell line and clone to accomplish this result. Furthermore, if the full length BChE is made, the cells produce a mixture of monomer, dimer and tetramer so that the present invention also provides a means of producing preferably the monomeric form.

BRIEF SUMMARY OF THE INVENTION

In one aspect, the present invention relates to an isolated nucleic acid, which may be DNA, such as a cDNA, or RNA, that encodes a polypeptide having BChE enzyme activity (as determined, for example, using the well known Ellman assay), wherein the nucleic acid has been codon-optimized, such as where the percentage of guanine plus cytosine (G+C) nucleotides in the coding region of the nucleic acid is greater than about 40%, or is greater than 45%, or is greater than 50%, or is greater than 55%, or is at least 60%, or is greater than 60% but not greater than 80%.

In specific embodiments, the isolated nucleic acid does not contain internal structural elements that reduce expression levels of the subject genetic construct, including an internal TATA-box, an internal ribosomal entry site, or a splice donor or acceptor site.

In one embodiment, the isolated nucleic acid of the invention contains or encodes at least one Kozak sequence, preferably upstream of the start site.

The isolated nucleic acid of the invention also encodes one or more glycosylation and/or sialylation sites on the synthesized polypeptide. In a preferred embodiment, these are sufficient in number to permit full glycosylation and/or sialylation of the encoded BChE.

BRIEF DESCRIPTION OF THE DRAWINGS

FIGS. 1-1 to 1-4 show codon optimized nucleotide (SEQ ID NO: 1) and corresponding amino acid (SEQ ID NO: 2) sequences of a BChE of the invention. Such sequences contain inserted restriction and other sites, such as the human signal or leader sequence made up of amino acids 1 to 21, where full length BChE begins with the sequence EDD starting at amino acid residue 22.

FIGS. 2-1 to 2-2 show nucleotide (SEQ ID NO: 5) and corresponding amino acid (SEQ ID NO: 6) sequences of native human BChE (i.e., without codon optimization), containing a goat casein leader or signal polypeptide (amino acids 1 to 15) for transgenic expression in goat's milk, and where the BChE native polypeptide begins with the sequence EDD starting at amino acid residue 17 (the glutamic acid numbered 1) and inserted arginine as 1').

FIGS. 3-1 to 3-4 show codon-optimized nucleotide (SEQ ID NO: 3) and amino acid sequence (SEQ ID NO: 4) of a BChE truncate of the invention, containing a human signal or leader sequence made up of amino acids 1 to 21, where the BChE truncate begins with the sequence EDD starting at amino acid residue 22.

DEFINITIONS

Unless expressly stated otherwise elsewhere herein, each of the following terms has the stated meaning:

The term "butyrylcholinesterase enzyme" or "BChE enzyme" means a polypeptide capable of hydrolyzing acetylcholine and butyrylcholine, and whose catalytic activity is inhibited by the chemical inhibitor iso-OMPA. Preferred BChE enzymes to be produced by the present invention are mammalian BChE enzymes. The term "BChE enzyme" also encompasses pharmaceutically acceptable salts of such a polypeptide.

The term "recombinant butyrylcholinesterase" or "recombinant BChE" means a BChE enzyme produced by a transiently transfected, stably transfected, or transgenic host cell or animal as directed by one of the expression constructs of the invention as well as by direct chemical synthesis. The term "recombinant BChE" also encompasses pharmaceutically acceptable salts of such a polypeptide.

The term "vector sequences" means any of several nucleic acid sequences established in the art which have utility in the recombinant DNA technologies of the invention to facilitate the cloning and/or propagation of the expression constructs including (but not limited to) plasmids, cosmids, phage vectors, viral vectors, and yeast artificial chromosomes.

The term "expression construct" or "construct" means a nucleic acid sequence comprising a target nucleic acid sequence or sequences whose expression is desired, operably linked to sequence elements which provide for the proper transcription and translation of the target nucleic acid sequence(s) within the chosen host cells. Such sequence elements may include a promoter, a signal sequence for secretion, a polyadenylation signal, intronic sequences, insulator sequences, and other elements described in the invention. The "expression construct" or "construct" may further comprise vector sequences.

The term "operably linked" means that a target nucleic acid sequence and one or more regulatory sequences (e.g., promoter or signal sequences) are physically linked so as to permit expression of the polypeptide encoded by the target nucleic acid sequence within a host cell.

The term "promoter" means a region of DNA involved in binding of RNA polymerase to initiate transcription.

The term "signal sequence" means a nucleic acid sequence which, when incorporated into a nucleic acid sequence encoding a polypeptide, directs secretion of the translated polypeptide (e.g., a BChE enzyme and/or a glycosyltransferase) from cells which express said polypeptide. The signal sequence is preferably located at the 5'-end of the nucleic acid sequence encoding the polypeptide, such that the polypeptide sequence encoded by the signal sequence is located at the N-terminus of the translated polypeptide, and is commonly a leader sequence. The term "signal peptide" means the peptide sequence resulting from translation of a signal sequence.

The term "host cell" means a cell which has been transfected with one or more expression constructs of the invention. Such host cells include mammalian cells in in vitro culture and cells found in vivo in an animal. Preferred in vitro cultured mammalian host cells include Per.C6 cells.

The term "transfection" means the process of introducing one or more of the expression constructs of the invention into a host cell by any of the methods well established in the art, including (but not limited to) microinjection, electroporation, liposome-mediated transfection, calcium phosphate-mediated transfection, or virus-mediated transfection. A host cell into which an expression construct of the invention has been introduced by transfection is "transfected". The term "transiently transfected cell" means a host cell wherein the introduced expression construct is not permanently integrated into the genome of the host cell or its progeny, and therefore may be eliminated from the host cell or its progeny over time. The term "stably transfected cell" means a host cell wherein the introduced expression construct has integrated into the genome of the host cell and its progeny.

In accordance with the present invention, the term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

"Isolated" in the context of the present invention with respect to polypeptides (or polynucleotides) means that the material is removed from its original environment (e.g., the natural environment if it is naturally occurring). For example, a naturally-occurring polynucleotide or polypeptide present in a living organism is not isolated, but the same polynucleotide or polypeptide, separated from some or all of the co-existing materials in the natural system, is isolated. Such polynucleotides could be part of a vector and/or such polynucleotides or polypeptides could be part of a composition, and still be isolated in that such vector or composition is not part of its natural environment. The polypeptides and polynucleotides of the present invention are preferably provided in an isolated form, and preferably are purified to homogeneity.

The term "coding region" refers to that portion of a gene which either naturally or normally codes for the expression product of that gene in its natural genomic environment, i.e., the region coding in vivo for the native expression product of the gene. The coding region can be from a normal, mutated or altered gene, or can even be from a DNA sequence, or gene, wholly synthesized in the laboratory using methods well known to those of skill in the art of DNA synthesis.

In accordance with the present invention, the term "nucleotide sequence" refers to a heteropolymer of deoxyribonucleotides. Generally, DNA segments encoding the proteins provided by this invention are assembled from cDNA fragments and short oligonucleotide linkers, or from a series of oligonucleotides, to provide a synthetic gene which is capable of being expressed in a recombinant transcriptional unit comprising regulatory elements derived from a microbial or viral operon.

The term "expression product" means that polypeptide or protein that is the natural translation product of the gene and any nucleic acid sequence coding equivalents resulting from genetic code degeneracy and thus coding for the same amino acid(s).

As used herein, the terms "portion," "segment," "truncate" and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to a polynucleotides, such terms refer to the products produced by treatment of said polynucleotides with any of the common endonucleases.

The term "fragment," when referring to a coding sequence, means a portion of DNA comprising less than the complete coding region whose expression product retains essentially the same biological function or activity as the expression product of the complete coding region.

The term "open reading frame (ORF)" means a series of triplets coding for amino acids without any termination codons and is a sequence (potentially) translatable into protein.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence.

In accordance with the present invention, the term "percent identity" or "percent identical," when referring to a nucleotide or amino acid sequence, means that the sequence is compared to a claimed or described sequence after alignment of the sequence to be compared (the "Compared Sequence") with the described or claimed sequence (the "Reference Sequence"). The Percent Identity is then determined according to the following formula:

Percent Identity=$100[1-(C/R)]$ wherein C is the number of differences between the Reference Sequence and the Compared Sequence over the length of alignment between these sequences wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the hereinabove calculated Percent Identity is less than the specified Percent Identity.

DETAILED DESCRIPTION OF THE INVENTION

Butyrylcholinesterase derived from human serum is a globular, tetrameric molecule with a molecular mass of approximately 340 kDa. Nine Asn-linked carbohydrate chains are found on each 574-amino acid subunit (which subunit begins with amino acid 17 in SEQ ID NO: 6). The tetrameric form of BChE is stable and has been preferred in the art for therapeutic uses. BChE enzymes produced according to the instant invention have the ability to bind and/or hydrolyze organophosphate, such as pesticides, and war gases, succinylcholine, or cocaine.

The BChE enzyme of the present invention comprises an amino acid sequence that is substantially identical to a sequence found in a mammalian BChE, more preferably, human BChE, and may be produced as a tetramer, a trimer, a dimer, or a monomer. In a preferred embodiment, the synthesized BChE of the invention has a glycosylation and/or sialylation profile that is substantially similar, if not identical, to that of native human BChE.

The BChE produced according to the present invention is preferably in monomeric form with high MRT, thus reducing the need for expensive post-synthetic modification to increase MRT, such as pegylation (i.e., attachment of one or more molecules of polyethylene glycol of varying molecular weight and structure). Conversely, BChE expressed recombinantly in CHO (Chinese hamster ovary) cells was found not to be mostly in the more stable tetrameric form, but rather consisted of approximately 55% dimers, 10-30% tetramers and 15-40% monomers (Blong, et al. Biochem. J., Vol. 327, pp 747-757 (1997)).

Recent studies have shown that a proline-rich amino acid sequence from the N-terminus of the collagen-tail protein caused acetylcholinesterase to assemble into the tetrameric form (Bon, et al. J. Biol. Chem. (1997) 272(5):3016-3021 and Krejci, et al. J. Biol. Chem. (1997) 272:22840-22847). To greatly increase the amount of monomeric BChE enzyme formed according to the invention, the DNA sequence encoding the BChE enzyme of the invention preferably does not comprise a proline-rich attachment domain (PRAD), which otherwise recruits recombinant BChE subunits (e.g., monomers, dimers and trimers) to form tetrameric associations.

The non-tetrameric forms of BChE are also useful in applications which do not require in vivo administration, such as the clean-up of lands used to store organophosphate compounds, as well as decontamination of military equipment exposed to organophosphates. For ex vivo use, these non-tetrameric forms of BChE may be incorporated into sponges, sprays, cleaning solutions or other materials useful for the topical application of the enzyme to equipment and personnel. These forms of the enzyme may also be applied externally to the skin and clothes of human patients who have been exposed to organophosphate compounds. The non-tetrameric forms of the enzyme may also find applications as barriers and sealants applied to the seams and closures of military clothing and gas masks used in chemical warfare situations.

The present invention also provides vectors that include polynucleotides of the present invention, host cells which are genetically engineered with vectors of the invention and the production of polypeptides of the invention by recombinant techniques.

Host cells are genetically engineered (i.e., transduced or transformed or transfected) with the vectors of this invention which may be, for example, a cloning vector or an expression vector, preferably in the form of a plasmid, a viral particle, a phage, etc. The engineered host cells can be cultured in conventional nutrient media modified as required for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention are preferably employed for producing polypeptides by recombinant techniques. Such a polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host cell.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (such as a promoter and/or enhancer, in either cis or trans location) to direct mRNA synthesis. As representative examples of such promoters, there may be mentioned: LTR or SV40 promoter, the phage lambda $P_L$ promoter and other promoters known to control expression of genes in eukaryotic, preferably human, cells. The expression vector also contains a ribosome binding site for translation initiation and a transcription terminator. The vector may also include appropriate sequences for amplifying expression, especially where these are designed to work optimally in human cells, for example, Per.C6 cells.

The vector containing the appropriate DNA sequence as herein described, as well as an appropriate promoter or control sequence, may be employed to transform an appropriate host to permit the host to express the protein.

As representative examples of appropriate hosts, there may be mentioned human cells, preferably Per.C6 cells (available from Percivia, Cambridge, Mass.).

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art and are commercially available.

Promoter regions can be selected from any desired gene using CAT (chloramphenicol transferase) vectors or other vectors with selectable markers. Two appropriate vectors are pKK232-8 and pCM7. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell is preferably a human cell, since the nucleic acids of the invention have been optimized for such human expression. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)). The constructs in host cells can be used in a conventional manner to produce the gene product encoded by the recombinant sequence. Alternatively, the polypeptides of the invention can be synthetically produced by conventional peptide synthesizers.

Appropriate cloning and expression vectors for use with eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes, especially human cells, is increased by inserting an enhancer sequence into the vector. Enhancers are cis-acting elements of DNA, usually from about 10 to about 300 by that act on a promoter to increase its transcription. Examples include the SV40 enhancer on the late side of the replication origin by 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification.

Mammalian, especially human, cell expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 splice, and polyadenylation sites may be used to provide the required non-transcribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

Because of the degeneracy of the genetic code, more than one codon may be employed to encode a particular amino acid. However, not all codons encoding the same amino acid are utilized equally. For optimal expression in a cell, e.g. a human cell, the nucleic acid, e.g. DNA, to be expressed may be codon optimized so as to contain a coding region utilizing the codons most commonly employed by that species or that particular type of cell. Codoh optimization is a technique which is now well known and used in the design of synthetic genes. Different organisms preferentially utilize one or other of these different codons. By optimizing codons, it is possible to greatly increase expression levels of the particular protein in a selected cell type.

In accordance with the foregoing, embodiments of an isolated nucleic acid of the invention have been codon-optimized, which codon optimization is expressed as a Codon Adaptation Index (CAI), wherein such CAI for nucleic acids of the invention is at least 0.7, preferably at least 0.8, more preferably at least 0.9, and most preferably at least 0.97. For wild-type (non-optimized human BChE gene), the CAI is at or about 0.69. Such Codon Adaptation Index is determined according to methods known in the art by setting the quality value of the most frequently used codon for a given amino acid in the desired expression system to 100 with the remaining codons scaled accordingly (see Sharp and Li, Nucleic Acids Research, Vol. 15(3), 99. 1281-1295 (1987)). The CAI uses a reference set of highly expressed genes from a species to determine relative merit of each codon to calculate a score for a gene from the frequency of use of all codons in said gene. This index is useful for predicting the level of expression of a gene and indicate likely success of heterologous gene expression in a given cell system.

In some embodiments, the nucleic acids, for example, a DNA, of the present invention have also been optimized using additional parameters. For example, analysis of the wild-type human BChE gene has been found to contain an average G+C content of about 40% by determining the GC content in a 40 bp window centered about various nucleotide positions. Conversely, the GC content of nucleic acids according to the present invention, such as the codon optimized nucleic acids disclosed herein, have an average GC content of about 60%. For example, in producing nucleic acids of the present invention, very high or low GC content has been avoided, so that any GC content less than 30% or above 80% has been avoided.

The present invention relates to an isolated nucleic acid, DNA or RNA, that encodes a polypeptide having BChE enzyme activity (for example, using the well known Ellman assay—Ellman, G. L., et al, Biochem. Pharmacol., Vol. 7, pp. 88-95 (1961)), wherein the percentage of guanine plus cytosine (G+C) nucleotides in the coding region of said nucleic acid is greater than 40%, or is greater than 45%, or is greater than 50%, or is greater than 55%, or is at least 60%, or is greater than 60% but is less than 80%. In all cases, codon usage has been adapted to the codon bias of human (Homo sapiens) genes.

Specific embodiments of an isolated nucleic acid of the invention include nucleic acids comprising a nucleotide sequence having at least 80% identity, or at least 90% identity, preferably at least 95% identity, more preferably at least 98% identity to the nucleotide sequence of SEQ ID NO: 1 or the complement thereof. In a preferred embodiment, the nucleic acid of the invention comprises, more preferably consists essentially of, and most preferably consists of, the nucleotide sequence of SEQ ID NO: 1 or the complement thereof. In all cases, such nucleic acids, in addition to SEQ ID NO: 1 itself, meet the other requirements of the invention regarding GC content and/or CAI and like parameters.

In one embodiment, the BChE polypeptide encoded by the nucleic acid of the invention comprises, preferably consists of, amino acids 22-564 of SEQ ID NO: 2. In some embodiments, the encoded BChE polypeptide contains fewer than the number of amino acids in SEQ ID NO: 2 (i.e., is a truncated, variant or modified form of said sequence, such as the truncate shown as SEQ ID NO: 4 and/or in FIG. 3, with or without the signal sequence). Such modification may affect the overall 3-dimensional structure or shape of the resulting BChE enzyme. Consequently, the resulting encoded polypeptide does not readily form tetramers or even dimers, but remains in a monomeric state.

In accordance with the invention, such monomeric BChE polypeptides are achieved by producing a BChE polypeptide that differs from the native BChE of SEQ ID NO: 6, or is a variant of such polypeptide, such as a polypeptide having less than 100% identity to the sequence of SEQ ID NO: 2 or 4 or amino acids 22-564 of said sequences but retaining substantially all of the BChE enzyme activity of said polypeptide, or where one or more amino acids present in such polypeptides are either different or not included in said polypeptide, which is thus a variant or shortened or truncated polypeptide and which forms mostly, or all, or only, monomers.

For example, such a truncate commonly differs from native, or full length, BChE (such as SEQ ID NO: 6 starting at amino acid 17) in that a specific domain is not present. In a preferred embodiment, such a domain (referred to in the art as the WAT domain) comprises the C-terminal portion of the BChE polypeptide, preferably the C-terminal 20 to 40 amino acids of a native BChE, more preferably the C-terminal 25 to 35 amino acids of native BChE, most preferably the C-terminal 31 amino acids of such BChE. To produce a truncate within the invention, any amino acid segment after the tryptophan residue at residue 564 of SEQ ID NO: 2 (FIG. 1) may be deleted from the sequence of the mature protein. In one embodiment, said BChE polypeptide does not form monomers because all or a portion of said WAT domain has been deleted or because one or more amino acid substitutions have been introduced into said domain to render it non-functional for the purpose of inducing multimer formation of the resulting mature polypeptide.

For expression from DNA, this is accomplished by insertion of a termination codon following the codon encoding such tryptophan, either immediately following it or following a codon. 3' of said tryptophan codon so as to subsequently shorten the resulting encoded amino acid sequence of the BChE protein. Where the latter is to be synthesized by direct chemical synthesis, the sequence from the N-terminus of SEQ ID NO: 2 up to or exceeding the tryptophan at residue 564 is included in the synthetic product but not some, most or all of the amino acids C-terminal of said tryptophan to form a truncate. BChE truncates of the present invention may or may not include a signal sequence, such as that shown in FIG. 1, 2 or 3. Thus, a truncate of the mature polypeptide is contemplated by the invention. One such example would consist of amino acids 22-564 of SEQ ID NO: 4.

Such a monomer, especially one composed of such a truncate, has the advantage of a much better defined amino acid sequence and is capable of being synthesized in amounts up to 10 times, 20 times or even 40 times, or more, the amounts normally synthesized of the tetrameric form of BChE and at greatly reduced cost, thereby making it a much more desirable therapeutic agent from both a clinical and commercial viewpoint.

The sequence KAGFHRWNNYMMDWKNQFNDYTSKKESCVGL (SEQ ID NO: 7), located at amino acid residues 565-595 of SEQ ID NO: 2, has been found to be involved in formation of multimeric BChE molecules, such as in the dimerization and/or tetramerization of BChE (see, for example, Blong et al., supra, which contains additional structural information concerning such domains). By the deletion of part or all of this domain, most, if not all, of the resulting BChE product is rendered not capable of forming multimers and so remains in monomic form. In forming such a truncate of the invention, only so much of this domain need be removed to prevent dimer or tetramer formation from the synthesized monomer. In one embodiment, such as SEQ ID NO: 4 (FIG. 3), all of it is missing. For such a product, the expression of the monomer is higher, the purification and characterization easier, and the cost of the product substantially lower.

In one preferred embodiment, this truncated form of BChE is expressed in Per.C6 cells with the optimal clone selected. This truncated BChE has a long MRT, making it the preferable form as a drug product. In other embodiments, such truncate is also prepared by direct synthesis and other means, such as using recombinant cells, preferably mammalian cells, more preferably human cells, most preferably Per.C6 (or PerC6) cells, that achieve high levels of glycosylation and/or sialylation of a heterologous protein, or where synthesis, either in vitro or in vivo, is followed by in vitro glycosylation and/or sialylation.

In a preferred embodiment, a BChE truncate of the invention comprises the amino acid sequence of SEQ ID NO: 4 (shown in FIG. 3), which comprises a human signal sequence at the N-terminus.

A BChE truncate of the present invention is thus a BChE molecule with part or all of the WAT domain removed. Without a functioning WAT domain, the molecule does not form multimers, such as tetramers and/or dimers, but forms mostly, if not only, monomers. The selection of the truncation site, for example, after W at 564 (of SEQ ID NO: 2, for example) facilitates a more uniform C-terminal region. Use of Per.C6 cells coupled with the selection of high glycosylation and high sialylation clone(s) ensures long serum half-life and is a preferred embodiment of the invention. In sum, such a truncated BChE construct is simple, results in higher yield, longer serum half-life and a more homogeneous product, meeting all the requirements needed for an effective pharmaceutical agent.

The BChE truncate of the present invention can be produced by any means known in the art, including by direct chemical synthesis and the sequence of such truncate, where prepared by expression of an encoding DNA, need not be derived from a codon-optimized DNA. Standard references are available that contain procedures well known in the art of molecular biology and genetic engineering for producing the nucleic acids and polypeptides of the present invention. Useful references include Sambrook, et al., Molecular Cloning: A Laboratory Manual, Second Edition, Cold Spring Harbor, N.Y., (1989), Wu et al, *Methods in Gene Biotechnology* (CRC Press, New York, N.Y., 1997), and *Recombinant Gene Expression Protocols*, in *Methods in Molecular Biology*, Vol. 62, (Tuan, ed., Humana Press, Totowa, N.J., 1997), the disclosures of which are hereby incorporated by reference.

In another aspect, the present invention relates to a vector comprising a nucleic acid of the invention, as well as to a recombinant cell containing such a vector and expressing a BChE polypeptide by expressing a nucleic acid of the invention, preferably where that nucleic acid is present in a vector of the invention. The present invention also relates to a method of preparing such a polypeptide having BChE enzyme activity, comprising expressing the polypeptide from a recombinant cell as described herein, preferably where the polypeptide comprises the amino acid sequence of SEQ ID NO: 4 (for example, SEQ ID NO: 2), including where the polypeptide forms only monomers, for example, where such polypeptide does not contain portions of one or more domains that promote formation of such supra-molecular structures, including where the entire domain is absent or sequence altered.

As noted above, monomers were thought to be less active that tetramers but this is likely due to improper glycosylation. The present invention provides a codon optimized nucleic acid encoding BChE and appropriate glycosylation sites coupled with a cell line especially useful for expressing the properly glycosylated truncated molecule as a fully active monomer monomer possessing good retention time.

A nucleic acid of the invention used to transform the cells useful in practicing the invention is a synthetic gene of which the nucleic acid of SEQ ID NO 1 is only a specific yet preferred example. Such nucleic acids include modified forms of SEQ ID NO: 1. The expression "modified form" refers to other nucleic acid sequences which encode BChE (including fragments or variants thereof) and have BChE enzyme activity but which utilize different codons, provided the requirement for the percentage GC content and other criteria recited in accordance with the invention are met. Suitable modified forms include those that comprise at least 80% identity, preferably at least 90% identity, more preferably at least 95% identity and even more preferably at least 98% identity to SEQ ID NO 1.

In one embodiment, the nucleic acid sequence of SEQ ID NO: 1 and/or SEQ ID NO: 3 have been codon-optimized for expression in human cells, such as Per.C6 cells (a fully characterized human cell line for use with recombinant adenoviral vectors (available from Crucell L.V., Leiden, The Netherlands). This cell line has the advantage of producing heterologous proteins in good yield. It has also been found to be free of prions, is easily transfected with exogenous genes and grows well in commercially available media free of animal and/or human derived proteins.

In addition to codon optimization, the different embodiments of the invention have been achieved by further optimizing the nucleic acids of the invention to avoid inclusion of polynucleotide sequence elements that would otherwise reduce expression of the nucleic acid, and subsequent synthesis of BChE. In particular said sequence elements may be selected from the group comprising; negative elements or repeat sequences, cis-acting motifs such as splice sites, internal TATA-boxes and ribosomal entry sites.

A TATA box (or TATA) site is well known in the art and generally represents a consensus sequence found in the promoter region of genes that are transcribed by the RNA polymerase II found in mammalian, such as human, cells. It is often located about 25 nucleotides upstream of the transcription start site (often having the sequence 5' TATAAAA 3' (SEQ ID NO: 11)). It is relevant in determining the initiation site for gene transcription. However, when such a site is present internally within the coding region of a gene it can adversely affect (i.e., slow) gene expression and is thus to be avoided where efficient high level expression is sought. Where possible, such sequences have been avoided in the nucleic acids of the present invention.

Gene expression is also slowed by other structural motifs found in coding regions of genes. One such motif is the chi-site, which can induce homologous recombination, thereby disrupting the cloned gene. For example, the enzyme RecBCD (a heterotrimeric helicase that initiates homologous recombination at double-stranded DNA breaks) can be modulated by the DNA sequence denoted "chi" (i.e., 5'-GCTGGTGG-3' (SEQ ID NO: 8)). Such chi-sites have been avoided, where possible, in achieving the nucleic acids of the present invention, which preferably neither contain nor encode such chi sites.

In eukaryotes, the Kozak sequences 5'-ACCACCAUGG-3' (SEQ ID NO: 9) or 5'-GCCACCAUGG-3' (SEQ ID NO: 10), which lie within a short 5' untranslated region, direct translation of mRNA and are thus upstream of the transcription start site (the AUG codon that begins transcription). These sequences are effectively recognized by the ribosome as a translation start site and are different from the internal ribosomal binding site (RBS), which includes an internal ribosomal entry site (IRES) or the 5' cap of the mRNA molecule. The strength of the Kozak sequence can determine the extent of translation of the mRNA and thus the amount of protein produced. Internal ribosomal entry sites have been avoided, where feasible, in achieving the nucleic acids of the invention. However, the nucleic acids, or genetic constructs, of the invention, for purposes of expression from recombinant cells of the invention, preferably do encode a Kozak site upstream of the start site.

Protein-coding genes of mammals may also contain introns that ate involved in RNA splicing events that take place after transcription is complete but prior to translation at the ribosome. Sequences of such sites are known in the art and have, where feasible, been avoided in designing the sequences of the nucleic acids of the invention, which are made up mostly of coding sequence and are thus cDNA in nature. For example, such a splice site may contain a an almost invariant GT sequence at the 5' end of the intron as part of a larger less conserved region. The 3' splice site or splice acceptor site terminates the intron with an almost always present AG sequence. Upstream of this AG site is often found a sequence in pyrimidine content (i.e., C and T nucleotides). Such structural motifs are well known in the art and, where feasible, have been likewise avoided in achieving the nucleic acids, or DNA constructs, of the present invention.

Recombinant butyrylcholinesterase forms often exhibit variation in the type of sugar residues found within the different sugars attached to the molecule. Such variation can negatively affect the mean retention time (MRT) of the BChE molecule in vivo. Among the factors that can determine such variability are the number and arrangement of non-sialylated galactose and mannose residues as well as the host cell used to produce the glycosylated final product in BChE expression, since different expression systems may glycosylate the BChE molecule differently. Processes of in vitro glycosylation after synthesis have been attempted by those in the art to avoid such problems. For example, it has been shown that the stability of BChE is affected by capping of the terminal carbohydrate residues with sialic acid since uncapped galactose residues bind to receptors on hepatocytes and thereby clear the protein from the system. The present invention preferably utilizes the Per.C6 expression system so as to achieve as close a similarity to the native human glycosylation patent for BChE as is possible.

What is claimed is:

1. An isolated nucleic acid that encodes a polypeptide having butyrylcholinesterase (BChE) enzyme activity, wherein the percentage of guanine plus cytosine (G+C) nucleotides in the coding region of said nucleic acid is greater than 40% but not greater than 80%, wherein said nucleic acid has at least 90% identity to the nucleotide sequence of SEQ ID NO: 1 and wherein the encoded polypeptide does not comprise a functional WAT domain.

2. The isolated nucleic acid of claim 1, wherein the percentage of guanine plus cytosine (G+C) nucleotides in the coding region of said nucleic acid is greater than 45% but not greater than 80%.

3. The isolated nucleic acid of claim 1, wherein the percentage of guanine plus cytosine (G+C) nucleotides in the coding region of said nucleic acid is greater than 50% but not greater than 80%.

4. The isolated nucleic acid of claim 1, wherein the percentage of guanine plus cytosine (G+C) nucleotides in the coding region of said nucleic acid is greater than 55% but not greater than 80%.

5. The isolated nucleic acid of claim 1, wherein the percentage of guanine plus cytosine (G+C) nucleotides in the coding region of said nucleic acid is greater than 60% but not greater than 80%.

6. The isolated nucleic acid of claim 1, wherein the percentage of guanine plus cytosine (G+C) nucleotides in the coding region of said nucleic acid is at least 60% but not greater than 80%.

7. The isolated nucleic acid of claim 1, wherein said nucleic acid does not contain or encode an internal TATA-box.

8. The isolated nucleic acid of claim 1, wherein said nucleic acid encodes one or more sialylation sites on said polypeptide.

9. The isolated nucleic acid of claim 1, wherein said nucleic acid does not contain or encode an internal ribosomal entry site.

10. The isolated nucleic acid of claim 1, wherein said nucleic acid does not contain or encode a splice donor or acceptor site.

11. The isolated nucleic acid of claim 1, wherein said nucleic acid contains or encodes at least one Kozak sequence upstream of the start site.

12. The isolated nucleic acid of claim 1, wherein the sequence of said nucleic acid has a Codon Adaptation Index (CAI) of at least 0.7.

13. The isolated nucleic acid of claim 1, wherein said nucleic acid has a CAI of at least 0.8.

14. The isolated nucleic acid of claim 1, wherein said nucleic acid has a CAI of at least 0.9.

15. The isolated nucleic acid of claim 1, wherein said nucleic acid has a CAI of at least 0.97.

16. The isolated nucleic acid of claim 1, wherein said percent identity is at least 95%.

17. The isolated nucleic acid of claim 1, wherein said percent identity is at least 98%.

18. The isolated nucleic acid of claim 1, wherein said nucleic acid is SEQ ID NO: 3.

19. The isolated nucleic acid of claim 1, wherein said BChE polypeptide consists of amino acids 22 to 564 of SEQ ID NO: 2.

20. The isolated nucleic acid of claim 1, wherein said BChE polypeptide consists of amino acids 1 to 564 of SEQ ID NO: 2.

21. The isolated nucleic acid of claim 1, wherein said encoded polypeptide contains one or more amino acid substitutions that render the WAT domain non-functional for the purpose of inducing multimer formation of the encoded polypeptide.

22. The isolated nucleic acid of claim 1, wherein said encoded polypeptide is missing all or a portion of the WAT domain.

23. An isolated fragment of the nucleic acid of claim 1, wherein said fragment encodes a polypeptide having BChE enzyme activity.

24. A vector comprising the nucleic acid of claim 1.

25. A recombinant cell containing the vector of claim 24.

26. A method of preparing a polypeptide having BChE enzyme activity, comprising expressing said polypeptide from the cell of claim 25.

27. The recombinant cell of claim 25, wherein said cell is a mammalian cell.

28. The recombinant cell of claim 25, wherein said cell is a human cell.

29. The recombinant cell of claim 25, wherein said cell is a Per.C6 cell.

30. The method of claim 26, wherein said polypeptide forms only monomers.

31. The method of claim 26, wherein said polypeptide does not contain all or a portion of the WAT domain.

32. The method of claim 31, wherein said polypeptide does not contain the WAT domain.

33. The method of claim 26, wherein said polypeptide does not contain all or a portion of the amino acid sequence of SEQ ID NO: 7.

34. The method of claim 26, wherein said polypeptide consists of amino acids 1 to 564 of SEQ ID NO: 2.

35. The method of claim 26, wherein said polypeptide consists of amino acids 22-564 of SEQ ID NO: 2.

36. The isolated nucleic acid of claim 1, wherein said nucleic acid is a DNA or the complement thereof.

37. The isolated nucleic acid of claim 36, wherein said DNA is a cDNA or the complement thereof.

38. The isolated nucleic acid of claim 1, wherein said nucleic acid isan RNA.

* * * * *